US012127796B2

(12) United States Patent
Malackowski et al.

(10) Patent No.: US 12,127,796 B2
(45) Date of Patent: *Oct. 29, 2024

(54) HIGH BANDWIDTH AND LOW LATENCY HYBRID COMMUNICATION TECHNIQUES FOR A NAVIGATION SYSTEM

(71) Applicant: Stryker Corporation, Kalamazoo, MI (US)

(72) Inventors: Donald W. Malackowski, Schoolcraft, MI (US); Paul Hoekstra, Kalamazoo, MI (US); Matt Shinew, Ada, MI (US); Chunwu Wu, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 1340 days.

This patent is subject to a terminal disclaimer.

(21) Appl. No.: 16/730,105

(22) Filed: Dec. 30, 2019

(65) Prior Publication Data
US 2020/0129245 A1 Apr. 30, 2020

Related U.S. Application Data

(63) Continuation of application No. 16/189,241, filed on Nov. 13, 2018, now Pat. No. 10,555,781.
(Continued)

(51) Int. Cl.
*A61B 34/20* (2016.01)
*A61B 34/30* (2016.01)
(Continued)

(52) U.S. Cl.
CPC .............. *A61B 34/20* (2016.02); *A61B 90/39* (2016.02); *G01C 21/1656* (2020.08);
(Continued)

(58) Field of Classification Search
CPC ......... A61B 34/20; A61B 90/39; A61B 34/30; A61B 2034/2048; A61B 2034/2055;
(Continued)

(56) References Cited

U.S. PATENT DOCUMENTS 6,434,480 B1 * 8/2002 Kubota ................ G08G 1/0962
7,158,118 B2 1/2007 Liberty
(Continued)

FOREIGN PATENT DOCUMENTS

DE 4225112 C1 12/1993
WO 2016081931 A1 5/2016

OTHER PUBLICATIONS

English language abstract and machine-assisted English translation for DE 42 25 112 extracted from espacenet.com database on Dec. 20, 2018, 11 pages.

*Primary Examiner* — Russell Frejd
*Assistant Examiner* — Ellis B. Ramirez
(74) *Attorney, Agent, or Firm* — Howard & Howard Attorneys PLLC

(57) ABSTRACT

Disclosed is a navigation system configured to track an object. The navigation system comprises a tracker configured to couple to the object and a localization device configured to track the tracker. The tracker and the localization device are configured to wirelessly communicate using a first communication method operable on a first spectrum and to wirelessly communicate using a second communication method operable on a second spectrum different from the first spectrum. The localization device utilizes the first communication method to track the tracker and utilizes the first communication method to manage an operating parameter of the tracker with respect to the second communication method.

22 Claims, 8 Drawing Sheets

Related U.S. Application Data

(60) Provisional application No. 62/586,340, filed on Nov. 15, 2017.

(51) Int. Cl.
| | |
|---|---|
| *A61B 90/00* | (2016.01) |
| *G01C 21/16* | (2006.01) |
| *G01S 5/02* | (2010.01) |
| *G01S 5/16* | (2006.01) |
| *G01S 17/66* | (2006.01) |
| *G01S 17/86* | (2020.01) |
| *G08C 17/02* | (2006.01) |
| *G08C 23/04* | (2006.01) |
| *H04B 1/02* | (2006.01) |
| *H04B 10/114* | (2013.01) |
| *H04N 5/04* | (2006.01) |

(52) U.S. Cl.
CPC .............. *G01S 5/0294* (2013.01); *G01S 5/16* (2013.01); *G01S 17/66* (2013.01); *G01S 17/86* (2020.01); *H04B 1/02* (2013.01); *H04B 10/1141* (2013.01); *A61B 2034/2048* (2016.02); *A61B 2034/2055* (2016.02); *A61B 2034/2057* (2016.02); *A61B 2034/2068* (2016.02); *A61B 34/30* (2016.02); *A61B 2090/3945* (2016.02); *G08C 17/02* (2013.01); *G08C 23/04* (2013.01); *H04N 5/04* (2013.01)

(58) Field of Classification Search
CPC .... A61B 2034/2057; A61B 2034/2068; A61B 2090/3945; G01C 21/1656; G01S 5/0294; G01S 5/16; G01S 17/66; G01S 17/86; H04B 1/02; H04B 10/1141; G08C 17/02; G08C 23/04; H04N 5/04
USPC ....... 701/300; 340/854.1; 359/350; 600/424; 606/130
See application file for complete search history.

(56) References Cited

U.S. PATENT DOCUMENTS

| | | |
|---|---|---|
| 7,725,162 B2 | 5/2010 | Malackowski et al. |
| 7,942,745 B2 | 5/2011 | Ikeda et al. |
| 8,041,536 B2 | 10/2011 | Ohta |
| 8,295,909 B2 | 10/2012 | Goldbach |
| 8,805,528 B2 | 8/2014 | Corndorf |
| 9,008,757 B2 | 4/2015 | Wu |
| 9,220,573 B2 | 12/2015 | Kendrick et al. |
| 9,381,085 B2 | 7/2016 | Axelson, Jr. et al. |
| 9,480,534 B2 | 11/2016 | Bowling et al. |
| 9,642,529 B1 | 5/2017 | Siddiqui |
| 9,707,043 B2 | 7/2017 | Bozung |
| 9,794,942 B1 | 10/2017 | Arrakoski |
| 10,555,781 B2 | 2/2020 | Malackowski et al. |
| 2001/0034530 A1 | 10/2001 | Malackowski et al. |
| 2005/0131426 A1 | 6/2005 | Moctezuma de la Barrera et al. |
| 2005/0256391 A1 | 11/2005 | Satoh et al. |
| 2007/0081695 A1 | 4/2007 | Foxlin et al. |
| 2007/0225595 A1* | 9/2007 | Malackowski ......... A61B 5/064 |
| 2008/0200794 A1 | 8/2008 | Teichman et al. |
| 2012/0038549 A1 | 2/2012 | Mandella et al. |
| 2012/0083705 A1 | 4/2012 | Yuen et al. |
| 2013/0128054 A1* | 5/2013 | Densham ............... H04N 7/181 |
| 2013/0147838 A1 | 6/2013 | Small et al. |
| 2014/0200621 A1* | 7/2014 | Malackowski ......... A61B 34/20 |
| 2014/0276943 A1* | 9/2014 | Bowling ................ A61B 34/32 |
| 2014/0320667 A1 | 10/2014 | Densham et al. |
| 2015/0002507 A1 | 1/2015 | Ambrus et al. |
| 2016/0098095 A1 | 4/2016 | Gonzalez-Banos et al. |
| 2017/0245945 A1 | 8/2017 | Zuhars et al. |
| 2017/0311843 A1 | 11/2017 | Bailey et al. |
| 2017/0343361 A1 | 11/2017 | Kandangath et al. |
| 2017/0372524 A1 | 12/2017 | Hill |
| 2018/0064497 A1* | 3/2018 | Hussain ................ A61B 34/32 |
| 2018/0168750 A1 | 6/2018 | Staunton et al. |
| 2018/0325608 A1 | 11/2018 | Kang et al. |
| 2018/0325621 A1 | 11/2018 | Srimohanarajah et al. |
| 2019/0053858 A1* | 2/2019 | Kapoor ................ A61B 8/4254 |
| 2019/0192044 A1 | 6/2019 | Ravi et al. |
| 2019/0228859 A1 | 7/2019 | Moctezuma de la Barrera |

* cited by examiner

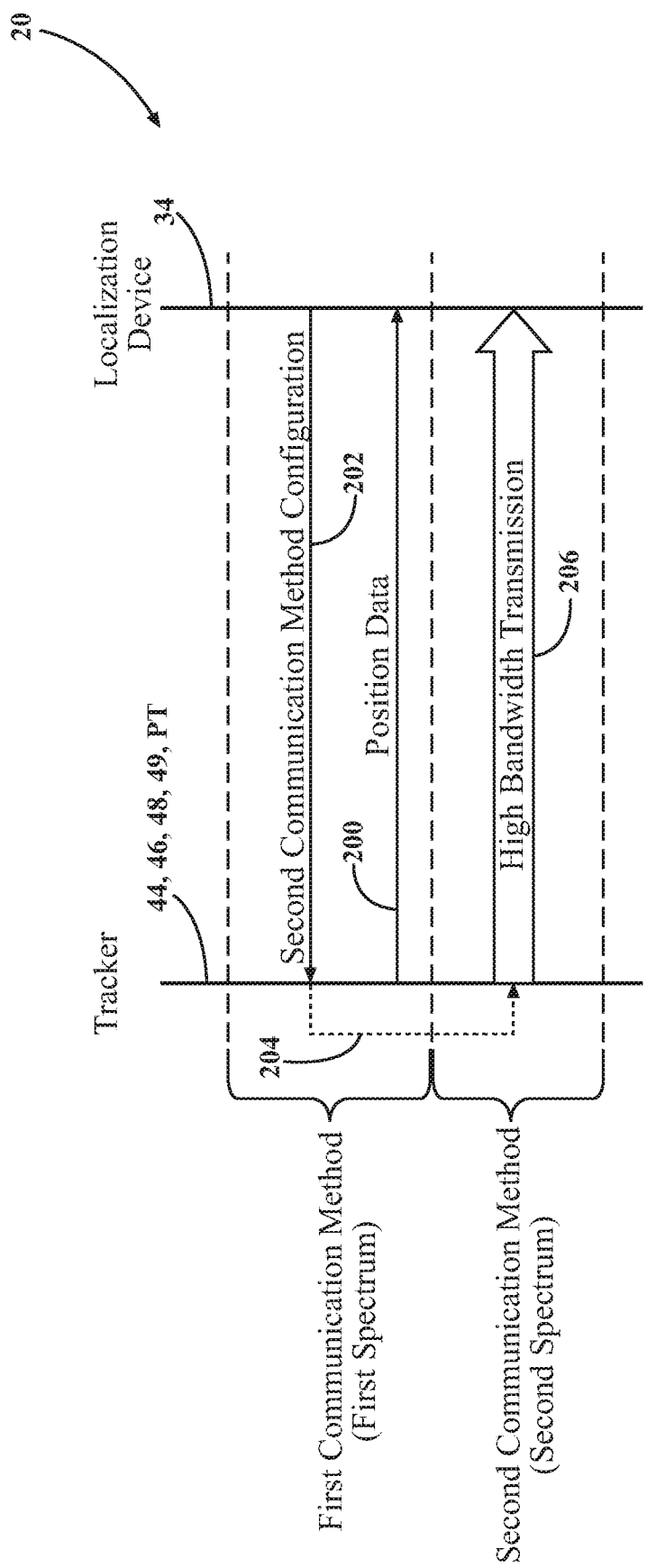

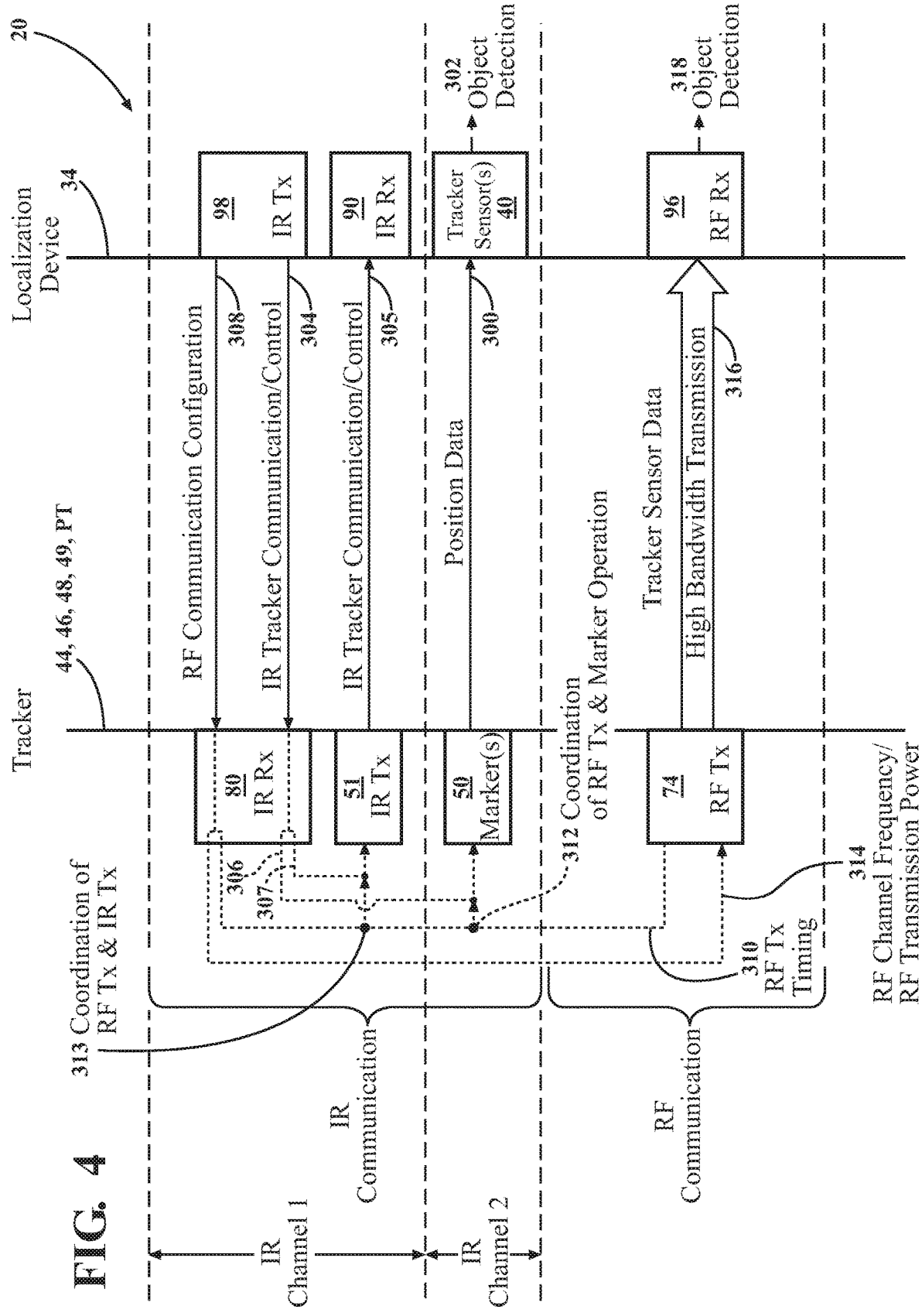

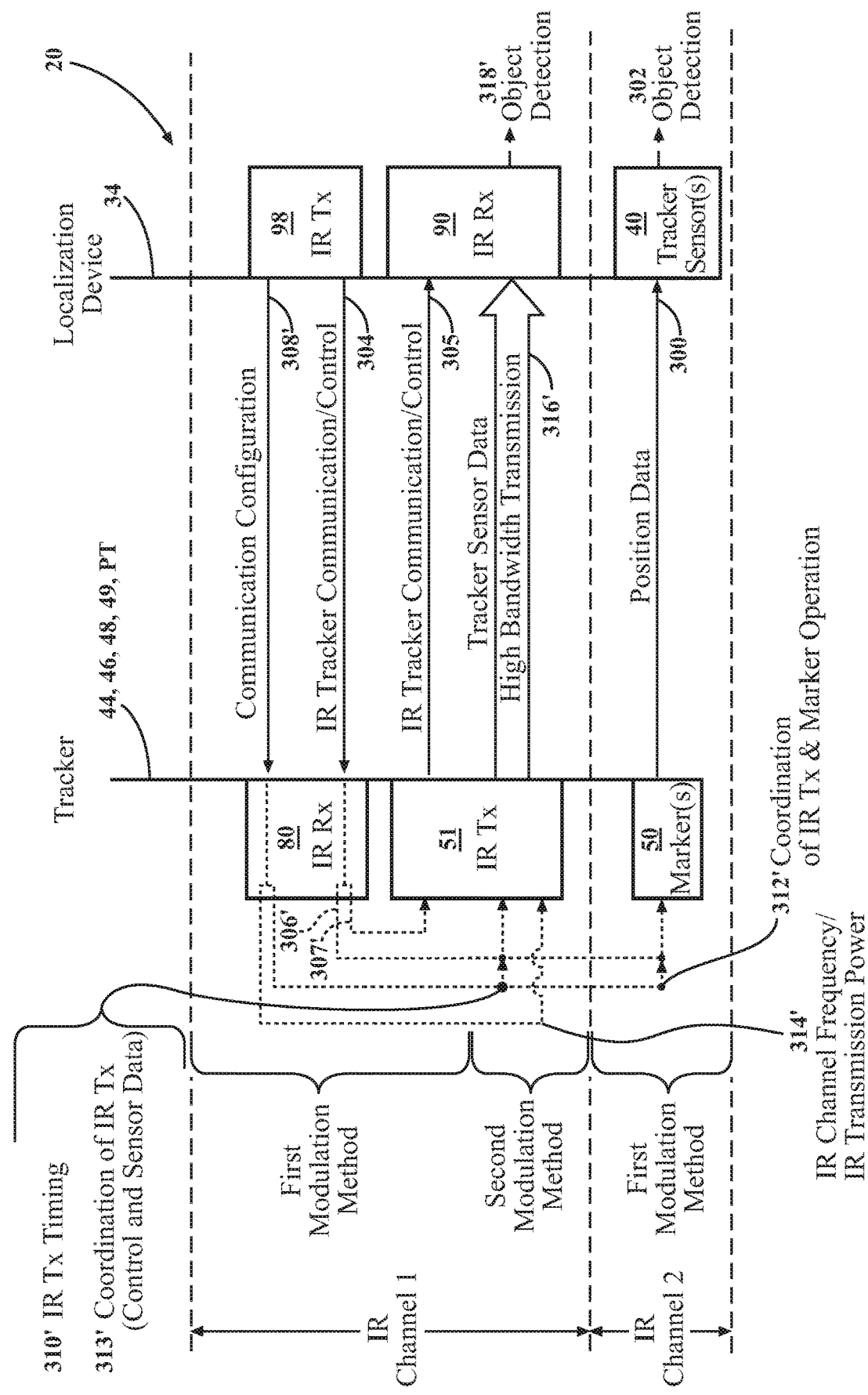

HIGH BANDWIDTH AND LOW LATENCY HYBRID COMMUNICATION TECHNIQUES FOR A NAVIGATION SYSTEM

CROSS-REFERENCE TO RELATED APPLICATIONS

The subject application is a continuation of U.S. Non-Provisional Patent App. No. 16/189,241, filed Nov. 13, 2018, which claims priority to and benefit of U.S. Provisional Patent Application No. 62/586,340, filed on Nov. 15, 2017, the entire disclosure of said applications being hereby incorporated by reference in their entirety.

TECHNICAL FIELD

The disclosure relates generally to a navigation system that tracks objects in space, and more specifically, techniques for improving bandwidth and latency for data transmission used by the navigation system.

BACKGROUND

Navigation systems assist users in precisely locating objects. For instance, navigation systems are used in industrial, aerospace, defense, and medical/surgical applications. In the surgical field, navigation systems assist surgeons in precisely placing surgical instruments relative to a patient's anatomy.

Surgeries in which navigation systems are used include neurosurgery and orthopedic surgery. Often the instrument and the anatomy are tracked together with their relative movement shown on a display. The navigation system may display the instrument moving in conjunction with a preoperative image or an intraoperative image of the anatomy.

Navigation systems often employ optical transmission means to track the pose of the instrument and anatomy. Optical navigation systems are widely used due to the accuracy of such systems.

Prior art optical navigation systems typically include optical trackers attached to the instrument and to the anatomy and a localization camera that includes one or more optical sensors for detecting light from the optical trackers. For instance, the optical trackers often include light emitting diodes (LEDs) that periodically transmit light to the optical sensors to enable the localization camera to determine the position of the LEDs.

The positions of the LEDs on the instrument tracker typically correlate to the coordinates of a working end of the instrument relative to a camera coordinate system. The positions of the LEDs on the anatomy tracker(s) typically correlate to the coordinates of a target area of the anatomy in three-dimensional space relative to the camera coordinate system. Thus, the position and/or orientation of the working end of the instrument relative to the target area of the anatomy can be tracked and displayed.

Two-way communication is often needed between the camera and instrument trackers for synchronization, command, control, and data exchange. This two-way communication must be low latency and deterministic for system accuracy and stability.

Recently, to improve such synchronization and control, optical trackers have been equipped with sensors, such as gyroscopes and accelerometers. These sensors are sometimes used to generate data relating to the rotational and translational movement of the instrument or the anatomy. Communication of such data to the localization camera requires high bandwidth. To accommodate high bandwidth transmission, prior techniques have connected the trackers to the localization camera system using a cable physically connected between each tracker and the localization camera.

There is an increasing desire to provide trackers that can wirelessly communicate sensor data to the localization camera. However, prior attempts have failed to provide a robust solution for such wireless transmission, particularly considering that two-way communication must be low latency and deterministic. Some prior systems utilize two-way infrared (IR) communication between the trackers and the localization camera. Although IR communication is highly accurate, IR communication is slow and often restricted by physical limitations such as line-of sight issues, and the like. Furthermore, in such techniques, IR communication occurs on the same spectrum as localization communication thereby causing interference. Therefore, IR communication, alone, is not suitable to communicate data wirelessly to the localization camera in a high-speed, low latency and deterministic fashion.

Another technique to communicate data wirelessly is radio frequency (RF) communication. Although RF communication is faster than IR communication, RF communication is not as robust as IR communication. For example, RF communication is often subject to electromagnetic interference from nearby devices or objects. Furthermore, RF communication often occurs over networks such as Wi-Fi, which are subject to significant latency. Additionally, using RF communication in a bi-directional fashion consumes much bandwidth due to the time required to switch communication directions. Certain types of RF communication, such as Bluetooth, often require many steps for pairing devices. Even when paired, such RF communication methods are commonly affected by pairing errors. Therefore, RF communication, alone, is also not well suited to communicate data wirelessly to the localization camera in a high-speed, low latency, and deterministic fashion.

Accordingly, prior attempts have failed to provide a robust method of command and control to wireless trackers being tracked by a localization camera as well as a high-speed, low latency method of transmitting data back the localization camera. There is a need to address at least the aforementioned issues of the prior art.

SUMMARY

One embodiment of a navigation system for tracking an object is provided. The navigation system comprising: a tracker configured to couple to the object; and a localization device configured to track the tracker; wherein the tracker and the localization device are configured to wirelessly communicate using a first communication method operable on a first spectrum and to wirelessly communicate using a second communication method operable on a second spectrum different from the first spectrum and wherein the localization device is configured to utilize the first communication method to track the tracker and to utilize the first communication method to manage an operating parameter of the tracker with respect to the second communication method.

One embodiment of a method of operating a navigation system is provided. The navigation system is configured to track an object, and comprises a tracker configured to couple to the object and a localization device configured to track the tracker, wherein the tracker and the localization device are configured to wirelessly communicate using a first communication method operable on a first spectrum and to wirelessly communicate using a second communication method operable on a second spectrum different from the first spectrum, the method comprising the steps of: utilizing, with the localization device, the first communication method to track the tracker; and utilizing, with the localization device, the first communication method to manage an operating parameter of the tracker with respect to the second communication method.

The systems, methods and techniques described herein for the above embodiments address issues of the prior art by providing high-speed, low latency and deterministic communication between the localization device and tracker, thereby improving system accuracy and stability. The techniques utilize two different communication methods for wirelessly communicating with the tracker without requiring a cable physically connected between the tracker and the localization device. In turn, the surgical workspace is less cluttered by cables.

Furthermore, by utilizing the first communication method to manage an operating parameter of the tracker with respect to the second communication method, the techniques described herein free-up bandwidth for the second communication method. Freeing up bandwidth for the second communication method enables high-speed wireless transmission of data between the localization device and the tracker. Such data can be, for example, sensor data, which often requires much bandwidth.

In turn, the systems, methods and techniques described herein for the above embodiments exploit the advantages of different communication methods to provide robust command and control to wireless trackers that are being tracked by the localization device as well as a high-speed, low latency method of reporting data back the localization device.

BRIEF DESCRIPTION OF THE DRAWINGS

Advantages of the present invention will be readily appreciated as the same becomes better understood by reference to the following detailed description when considered in connection with the accompanying drawings wherein:

FIG. 3 is a method sequence diagram illustrating events/transmissions performed by the localization device and/or the tracker in accordance with hybrid communication techniques described herein.

FIG. 4 is a method sequence diagram illustrating events/transmissions performed by the localization device and/or the tracker in accordance with one example of a hybrid IR/RF communication technique described herein.

FIGS. 6 and 7 are method sequence diagrams illustrating events/transmissions performed by the localization device and/or the tracker in accordance with dual modulation communication techniques.

DETAILED DESCRIPTION

I. System Overview

Figure 1:
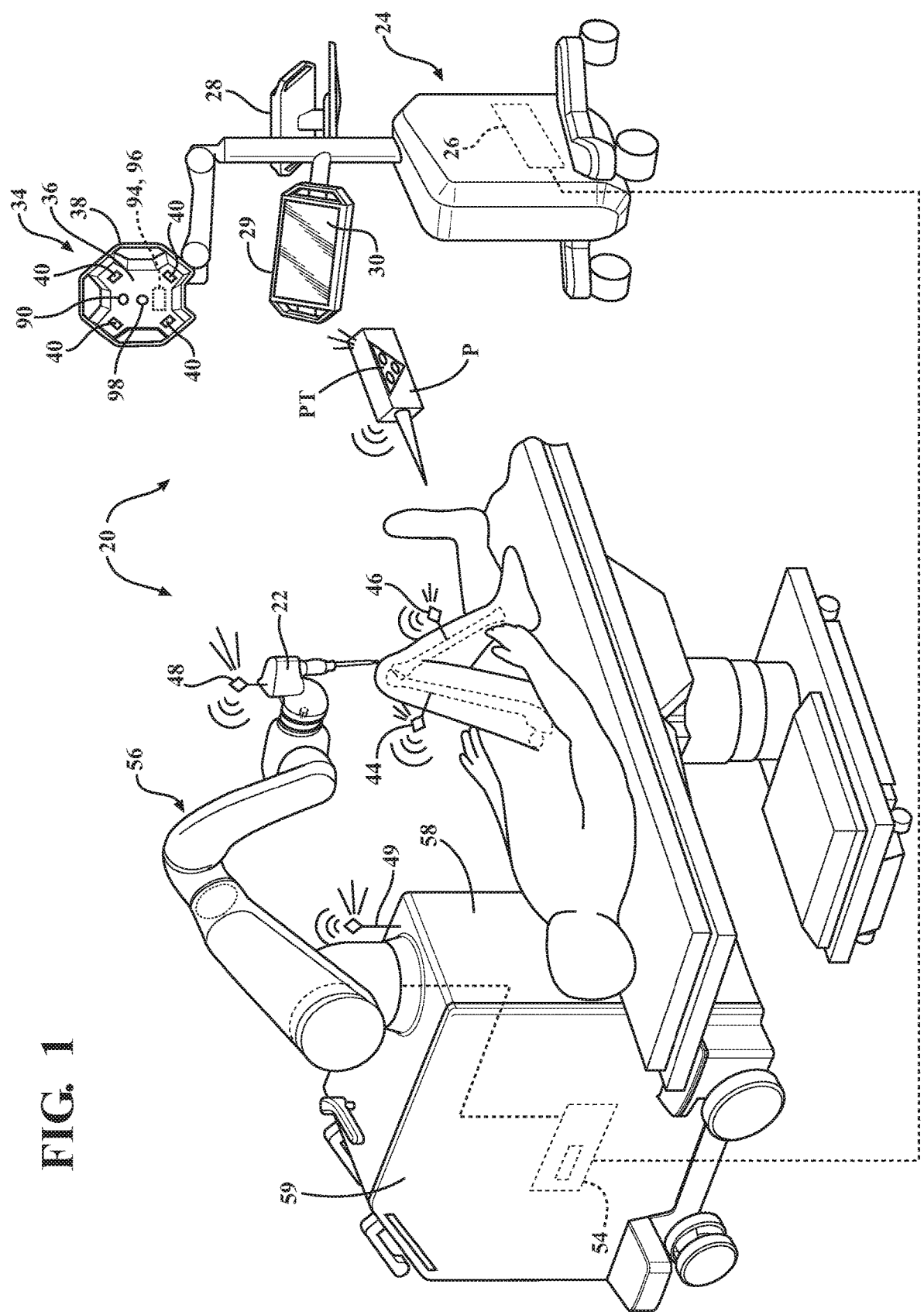
FIG. 1 is a perspective view of one example of a navigation system including a localization device for wirelessly tracking a plurality of objects using trackers.

Referring to FIG. 1, one example of a navigation system 20 for tracking an object is illustrated. The navigation system 20 is shown in a surgical setting such as an operating room of a medical facility. For surgical applications, the navigation system 20 is configured to track movement of various objects in the operating room. Such objects include, for example, an anatomy (e.g., femur and tibia) of a patient, an instrument 22, such as a surgical instrument, a pointer (P) instrument, a robotic manipulator base 58, or any other component or subject of a surgical system. The navigation system 20 tracks these objects for purposes such as controlling the instrument 22, and in some cases, controlling or constraining movement of the instrument 22 relative to a predefined path or anatomical boundary. The navigation system 22 may display a tracked position and orientation of the object to the surgeon.

In the embodiment shown, the instrument 22 is an end effector of a robotic manipulator 56. The instrument 22 of the robotic manipulator 56 may be used for cutting away material from a patient's anatomy, such as bone or soft tissue. Such an arrangement is shown in U.S. patent application Ser. No. 13/958,834, entitled, "Navigation System for use with a Surgical Manipulator Operable in Manual or Semi-Autonomous Mode", the disclosure of which is hereby incorporated by reference.

The navigation system 20 and robotic manipulator 56, and techniques for controlling the instrument 22 can be like those described in U.S. patent application Ser. No. 15/840,278, entitled "Techniques for Modifying Tool Operation in a Surgical Robotic System Based on Comparing Actual and Commanded States of the Tool Relative to a Surgical Site," the entire disclosure of which is hereby incorporated by reference in its entirety.

In other systems, the instrument 22 has a cutting tool that is movable in three degrees of freedom relative to a handheld housing and is manually positioned by the hand of the surgeon, without the aid of cutting jig, guide arm or other constraining mechanism, such as a manipulator or robot. Such a surgical instrument is described in U.S. patent application Ser. No. 13/600,888, entitled "Surgical Instrument Including Housing, a Cutting Accessory that Extends from the Housing and Actuators that Establish the Position of the Cutting Accessory Relative to the Housing", hereby incorporated by reference.

The instrument 22 can be used to prepare bone for surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation", the disclosure of which is hereby incorporated by reference.

In the example shown, the navigation system 20 includes a computer cart assembly 24 that houses a navigation computer 26. One or more navigation interfaces are in operative communication with the navigation computer 26. In one example, the navigation interfaces include a display 28 adapted to be situated outside of the sterile field and a display 29 adapted to be situated inside the sterile field. The displays 28, 29 are adjustably mounted to the computer cart assembly 24. One or more input devices 30 can be used to input information into the navigation computer 26 or otherwise select/control certain aspects of the navigation computer 26. In the example of FIG. 1, the input device 30 is a touchscreen device. However, other input devices 30 are fully contemplated, such as a mouse, keyboard, voice-activation device, gesture control device, etc.

The navigation system 20 may include a camera unit 36 for facilitating wireless reception/transmission of signals for localization/tracking. The camera unit 36 has an outer casing 38 that houses various components, as will be described below. The computer cart assembly 24, display 28, and camera unit 36 may be like those described in U.S. Pat. No. 7,725,162 to Malackowski, et al. issued on May 25, 2010, entitled "Surgery System", hereby incorporated by reference.

The navigation system 20 includes a localization device 34 and one or more trackers 44, 46, 48, 49, PT. The trackers 44, 46, 48, 49, PT are configured to couple to, attach to, or otherwise be integrated with the object being tracked. The navigation system 20 uses the localization device 34 to track the position and/or orientation of one or more of the trackers 44, 46, 48, 49, PT. In turn, the navigation system 20 is able to track the respective object by tracking the position and/or orientation of the respective tracker 44, 46, 48, 49, PT.

The localization device 34 communicates with the navigation computer 26. For example, position and orientation signals, control signals, and/or data are transmitted to/from the navigation computer 26 from/to the trackers 44, 46, 48, 49, PT for purposes of tracking the objects. The navigation computer 26 can be a personal computer or laptop computer. Navigation computer 26 has a central processing unit (CPU) and/or other processors as well as non-transitory computer memory. The navigation computer 26 may be loaded with software modules, as described below. The software modules convert the signals received from the camera unit 36 into data representative of the position and/or orientation of the objects being tracked.

In the illustrated embodiment of FIG. 1, one tracker 44 is coupled to the femur of the patient and another tracker 46 is coupled to the tibia of the patient. Trackers 44, 46 may be firmly affixed to sections of bone. Trackers 44, 46 may be attached to the bone in the manner shown in U.S. Pat. No. 7,725,162, hereby incorporated by reference. In further embodiments, an additional tracker (not shown) is coupled to the patella to track a position and orientation of the patella. In further embodiments, the trackers 44, 46 could be mounted to other tissue types or parts of the anatomy.

An instrument tracker 48 may be coupled to the instrument 22. The instrument tracker 48 may be integrated into the instrument 22 during manufacture or may be separately mounted to the instrument 22 in preparation for a procedure. A working end of the instrument 22 may be the subject of tracking, and may be a rotating bur, sagittal saw, electrical ablation device, or the like.

Tracker 49, if present, may be coupled a base 58 of the robotic manipulator 56. The base 58 is generally a portion of the robotic manipulator 56 that is stationary during usage thereby providing a fixed reference coordinate system (i.e., a virtual zero pose) for other components of the robotic manipulator 56 or the system in general. In this example, the base 58 may be defined with respect to a manipulator cart 59, such as where the robotic manipulator 56 is physically attached to the cart 59. Examples of a tracker for the base 58 of the robotic manipulator 56 can be like those described in U.S. patent application Ser. No. 15/840,278 entitled "Techniques for Modifying Tool Operation in a Surgical Robotic System Based on Comparing Actual and Commanded States of the Tool Relative to a Surgical Site," the entire disclosure of which is hereby incorporated by reference in its entirety.

A tracker PT may be coupled to a pointer instrument P, such as disclosed in U.S. Pat. No. 7,725,162 to Malackowski, et al., hereby incorporated by reference. The pointer instrument P may be used to map the anatomy coordinate system to pre-operative images for registration purposes.

Any of the trackers 44, 46, 48, 49, PT can be self-powered with an internal power supply or may receive power through the host object, if available. Trackers other than the trackers 44, 46, 48, 49, PT specifically shown in the figures are fully contemplated. Such other trackers may be provided for purposes of tracking any object other than those shown in FIG. 1. For example, such objects may be objects to be avoided during surgery.

In one embodiment, the localization device 34 and the trackers 44, 46, 48, 49, PT are in wireless communication with one another. In other words, any data/signals transmitted to the localization device 34 from any of the trackers 44, 46, 48, 49, PT, or vice-versa, are transmitted wirelessly, without cable connection between the localization device 34 and the trackers 44, 46, 48, 49, PT. In some instances, however, wired, cable connection may be utilized in addition to wireless communication.

Figure 2:
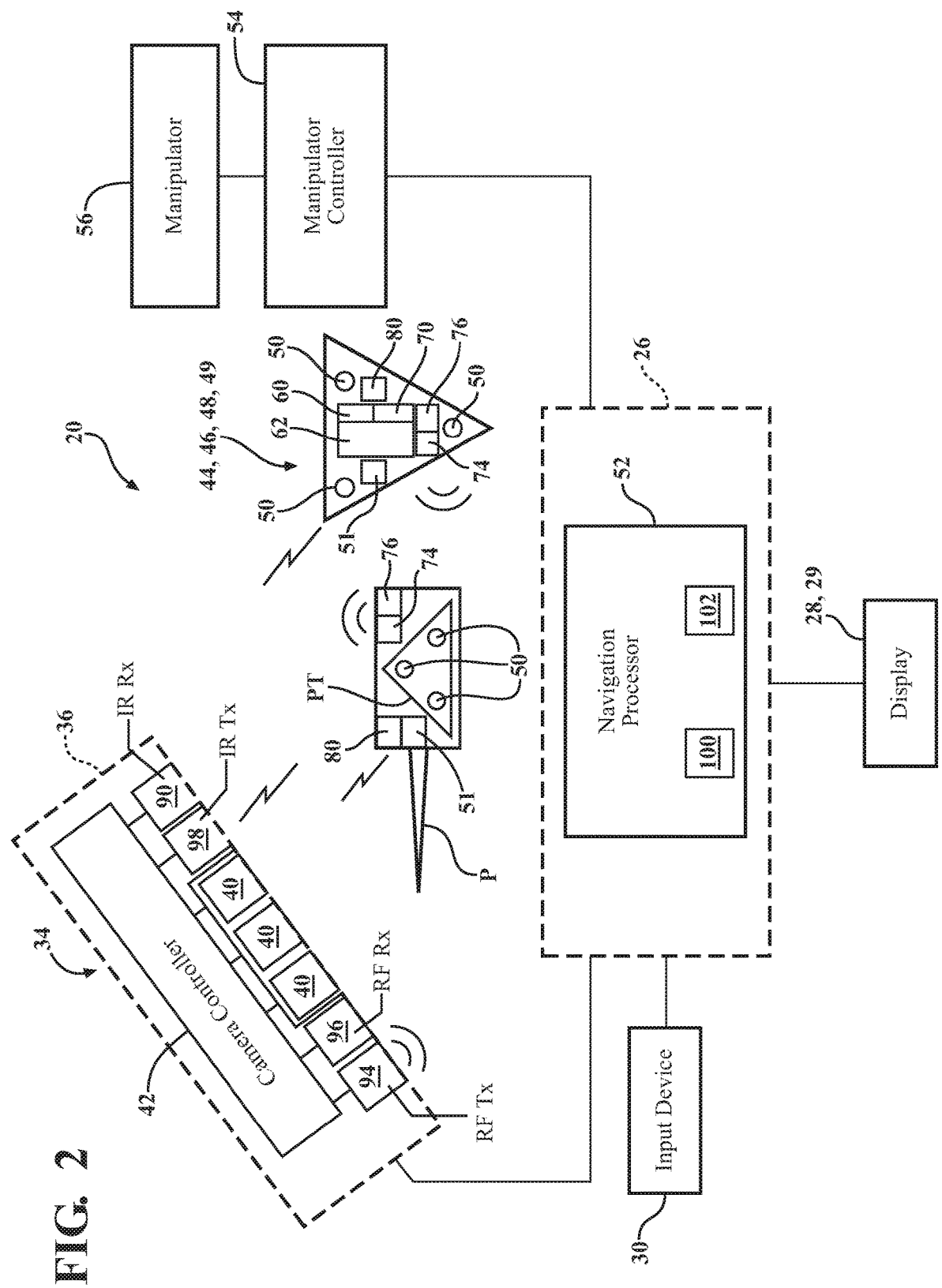
FIG. 2 is a block diagram of the navigation system of FIG. 1 wherein the localization device and the trackers comprise components for implementing hybrid IR/RF communication and control.

With reference to FIGS. 1 and 2, the localization device 34, according to one example, includes tracking sensors 40 for tracking the respective positions of the trackers 44, 46, 48, 49, PT. In one example, the tracking sensors 40 are embodied by the camera unit 36. The camera unit 36 includes one or more tracking sensors 40. The tracking sensors 40 are configured to detect the position of tracking markers 50 of the respective trackers 44, 46, 48, 49, PT. The camera unit 36 may include any number of tracking sensors 40. In some embodiments, at least two tracking sensors 40 are employed. The tracking sensors 40 may be separate high-resolution charge-coupled devices (CCD). In one embodiment three, one-dimensional CCDs are employed. In other embodiments, separate camera units, each with a separate CCD, or two or more CCDs, could also be arranged around the operating room. The tracking sensors 40 may be positioned in areas other than on the camera unit 36.

In one embodiment, the tracking sensors 40 are optical sensors, and more specifically, IR sensors. Each of the tracking sensors 40 is configured to detect IR signals through the IR spectrum. The localization device 34 may comprise configurations or devices for detecting IR signals for tracking purposes using devices other than optical sensors or CCDs.

The camera unit 36 may be mounted on an adjustable arm to position the tracking sensors 40 above a zone in which the procedure is to take place to provide the camera unit 36 with a field of view that is ideally free from obstructions. An unobstructed field of view helps the camera unit 36 detect trackers 44, 46, 48, 49 without interference. The localization device 34, and components thereof, may be embodied in a configuration physically and functionally different from that shown in FIG. 1.

The trackers 44, 46, 48, 49, PT may include one or more tracking markers 50. The tracking markers 50 may be passive, active, or combinations thereof. The tracking sensors 40 of the localization device 34 receive reflected or radiated light signals from tracking markers 50 of any of the trackers 44, 46, 48, 49, PT for tracking the same. Any number of tracking markers 50 may be utilized for any given tracker 44, 46, 48, 49, PT. Examples of active tracking markers 50 include, but are not limited to IR emitters, e.g., IR emitting LEDs, or the like. In one embodiment, at least three active tracking markers 50 are used for a tracker. The active tracking markers 50 may be sequentially fired, for transmitting light signals to the tracking sensors 40.

Examples of passive tracking markers 50 include reflective elements to reflect light radiated from the tracking sensors 40, or the like. The reflected light is then received by the tracking sensors 40 for tracking purposes.

The tracking sensors 40 may have sampling rates in excess of 100 Hz, 300 Hz, or 500 Hz. In some embodiments, the tracking sensors 40 have sampling rates of 1000 Hz. The sampling rate is the rate at which the tracking sensors 40 receive light signals from sequentially fired tracking markers 50. The signals from the tracking markers 50 may be fired at different rates for each tracker. IR signals can be sent every frame or frame groups (e.g., every 10 frames) for higher localization rates.

Techniques for utilizing a localizer for tracking the position of trackers can be like those described in U.S. patent application Ser. No. 13/958,834, entitled, "Navigation System for use with a Surgical Manipulator Operable in Manual or Semi-Autonomous Mode", the disclosure of which is hereby incorporated by reference.

II. Hybrid Wireless Communication and Control Techniques

Although the techniques described herein may be utilized with any one or more of the trackers 44, 46, 48, 49, PT, the description below refers to the instrument tracker 48 for simplicity in description.

In addition to the tracking techniques described above, the tracker 48 and the localization device 34 are configured to wirelessly communicate using a first communication method or link. The term "communication method" refers to a type of communication as defined by the electromagnetic spectrum. The electromagnetic spectrum includes a radio (wave) spectrum defined approximately between 3 Hz to 300 MHz, a microwave spectrum defined approximately between 300 MHz to 300 GHz, an infrared spectrum defined approximately between 300 GHz and 430 THz, etc. The first communication method is operable on one of these spectrums. As such, the first communication method may comprise radio frequency (RF) communication, microwave communication, or infrared (IR) communication.

In one embodiment, the first communication method comprises IR communication such that the tracker 48 and the localization device 34 wirelessly communicate using IR communication. In this embodiment, the tracker 48 and the localization device 34 are equipped with components to enable IR communication. Of course, where the first communication method is other than IR (as will be described below), the tracker 48 and the localization device 34 may be alternatively, or additionally be equipped with components to enable such other methods of communication.

In this embodiment, the localization device 34 may comprise one or more IR receivers 90 (IR Rx), which may be housed by a camera unit 36, as shown in FIGS. 1 and 2. The IR receiver 90 may located in areas other than on the camera unit 36. The IR receiver 90 enables IR communication with the tracker 48. The IR receiver 90 is configured to wirelessly receive IR signals and data from the tracker 48 over the IR spectrum. For example, the IR receiver 90 may comprise Light Emitting Diode (LED) IR detectors, photodetectors, and the like.

The localization device 34 may include an IR transmitter 98 (IR Tx) for transmitting signals or data using IR communication. The IR transmitter 98 may be housed by the camera unit 36 or may be located elsewhere. The IR transmitter 98 is configured to wirelessly transmit IR signals to the tracker 48 over the IR spectrum. The IR transmitter 98 may comprise one or more IR emitters, such as IR emitting LEDs, or the like. The IR transmitter 98 may include any number of IR emitters.

In some embodiments, the IR receiver 90 and the IR transmitter 98 are embodied as separated devices. Alternatively, the IR receiver 90 and the IR transmitter 98 may be combined into a single IR transceiver that performs all IR transmission and IR reception for the localization device 34. In some embodiments, the tracking sensors 40 may supplement or implement the IR receiver 90. Moreover, the IR receiver 90 may supplement the tracking sensors 40 for tracking the position of the tracker 48.

With respect to the tracker 48, IR communication with the localization device 34 may be enabled by providing the tracker 48 with an IR transmitter 51 (IR Tx) and an IR receiver 80 (IR Rx). The IR transmitter 51 and IR receiver 80 are coupled to, attached to, or otherwise integrated with the tracker 48.

The IR receiver 80 of the tracker 48 is configured to wirelessly receive IR signals from the IR transmitter 98 of the localization device 34 over the IR spectrum. The IR receiver 80 of the tracker 48 may include one or more optical sensors, such as LED IR detectors, photodetectors, CCDs, or the like. The IR receiver 80 of the tracker 48 may comprise configurations for detecting IR signals other than tracking sensors 40 or CCDs.

The IR transmitter 51 of the tracker 48 is configured to wirelessly transmit IR signals to the IR receiver 90 of the localization device 34 over the IR spectrum. The IR transmitter 51 of the tracker 48 may comprise one or more IR emitters, such as IR emitting LEDs, or the like. The IR transmitter 51 may include any number of IR emitters. In some embodiments, the active tracking markers 50 may supplement or implement the IR transmitter 51.

The IR transmitter 51 is connected to a tracker controller 62 located in a housing (not shown) of the associated tracker 48. The tracker controller 62 may comprise any suitable microcontroller, processor, integrated circuits, and the like, for executing functionality of the tracker 48 described herein. The tracker controller 62 may be coupled to a tracker memory, which may store data related to the tracker 48, and software instructions, which may be executed by the tracker controller 62.

Pairing between the localization device 34 and the tracker 48 can be performed using IR communication. Such pairing can be done automatically and in a robust fashion, because IR signals remain in the general area in which they are transmitted. IR communication between the localization device 34 and the tracker 48 can be master-slave, time synchronized, or a combination of both.

Aspects of command, control, and other data exchange between the tracker 48 and the localization device 34 using wireless IR communication are described in detail below.

In addition to communicating using the first communication method, the tracker 48 and the localization device 34 are configured to wirelessly communicate using a second communication method or link. The second communication method is similarly a type of communication as defined by the electromagnetic spectrum. However, the second communication method is different from the first communication method. In other words, the second communication method is operable on a second spectrum different from the first spectrum of the first communication method. Thus, the first and second communication methods can co-exist without interfering with one another.

Thus, for example, if the first communication method is IR communication, the second communication method can be RF communication or microwave communication. Alternatively, if the first communication method is RF communication, the second communication method can be IR communication or microwave communication, etc. As such, the navigation system 20 employs a multi or hybrid form of communication between the tracker 48 and the localization device 34.

Any of the communication methods described herein may include various channels operable on the respective spectrum. Thus, IR communication may occur on any one of a plurality of selectable IR channels on the IR spectrum, RF communication may occur on any one of a plurality of selectable RF channels on the RF spectrum, and microwave communication may occur on any one of a plurality of selectable microwave channels on the microwave spectrum. In one example, the channels for any given communication method are distinguished from one another by different frequencies within the respective spectrum. Examples of how these selectable channels may be utilized are described below.

Continuing with the example described above wherein the first communication is IR communication, the second communication method according to this embodiment comprises RF communication. As such, the tracker 48 and the localization device 34 also wirelessly communicate using RF communication. In this embodiment, the tracker 48 and the localization device 34 are equipped with components to enable RF communication over the RF spectrum.

Specifically, the localization device 34 may include an RF transmitter 94 (RF Tx) and an RF receiver 96 (RF Rx). The RF transmitter 94 is configured to wirelessly transmit RF signals to the tracker 48 over the RF spectrum. The RF receiver 96 is configured to wirelessly receive RF signals from the tracker 48 over the RF spectrum. The RF transmitter and receiver 94, 96 may utilize one or more antennas 112 (FIG. 5) to propagate and/or receive RF signals. In some embodiments, the RF transmitter and receiver 94, 96 are embodied as separated devices. Alternatively, the RF transmitter and receiver 94, 96 may be combined into a single RF transceiver that performs all RF transmission and reception for the localization device 34. The RF transmitter and receiver 94, 96 may be configured to communicate according to any suitable frequency or frequency range within the RF spectrum, such as frequencies in excess of 2.4 GHz.

The RF transmitter and receiver 94, 96 may be housed by the camera unit 36, as shown in FIG. 1. Because RF communication is not sensitive to line-of-sight issues like IR communication, the RF transmitter and receiver 94, 96 may be provided at locations other than at the camera unit 36. For instance, the RF transmitter and receiver 94, 96 may be coupled to the cart 24, and/or may be remotely coupled to the navigation computer 26 using any suitable wireless or wired connection.

With respect to the tracker 48, RF communication may be enabled by providing the tracker 48 with an RF transmitter 74 (RF Tx) and an RF receiver 76 (RF Rx), as shown in FIG. 2. The RF transmitter 74 and RF receiver 76 are coupled to, attached to, or otherwise integrated with the tracker 48.

The RF transmitter 74 of the tracker 48 is configured to wirelessly transmit RF signals to the localization device 34 over the RF spectrum. The RF receiver 76 of the tracker 48 is configured to wirelessly receive RF signals from the localization device 34 over the RF spectrum. The RF transmitter and receiver 74, 76 of the tracker 48 may utilize one or more antennas 110 (FIG. 5) to propagate and/or receive RF signals. In some embodiments, the RF transmitter and receiver 74, 76 are embodied as separated devices. Alternatively, the RF transmitter and receiver 74, 76 may be combined into a single RF transceiver that performs all RF transmission and reception for the tracker 48. The RF transmitter and receiver 74, 76 of the tracker 48 may be configured to communicate according to any suitable frequency or frequency range within the RF spectrum.

As will be understood from the examples below, such RF communication between the tracker 48 and the localization device 34 may be uni-directional (i.e., from the tracker 48 to the localization device 34) or may be bi-directional. Aspects of command, control, and other data exchange between the tracker 48 and the localization device 34 using wireless RF communication are described in detail below.

Although components of IR and RF communication have been described above, it should be understood that components for the tracker 48 and the localization device 34 for enabling microwave communication are fully contemplated, and such components include, but are not limited to microwave transmitters, microwave receivers, and microwave antennas.

As shown in FIG. 2, the localization device 34, and more specifically, the camera unit 36, includes a camera controller 42 in communication with and configured to control the tracking sensors 40, IR receiver and transmitter 90, 98 and the RF transmitter and receiver 94, 96 of the localization device 34. The camera controller 42 is configured to process IR signals received by the tracking sensors 40 and/or IR receiver 90, and to instruct transmission of IR signals from the IR transmitter 98. Similarly, the camera controller 42 is configured to process RF signals received by the RF receiver 96, and to instruct transmission of RF signals from the RF transmitter 94. The camera controller 42 may comprise a separate controller disposed remote from the localization device 34 in instances where the RF transmitter and receiver 94, 96 are remotely located.

The camera controller 42 may communicate with any of the aforementioned components of the localization device 34 using wired or wireless connection. In other embodiments, the aforementioned components may communicate directly with the navigation computer 26. The camera controller 42 communicates with the navigation computer 26 using wired or wireless connection. One such connection may be an IEEE 1394 interface, which is a serial bus interface standard for high-speed communications and isochronous real-time data transfer. Connection may also use a company specific protocol.

The tracker 48 comprises one or more sensors configured to generate data. In one example, the sensors are inertial sensors embodied as one or more gyroscope sensors 60 and/or one or more accelerometers 70. Other types of inertial sensors may be utilized. Examples of inertial sensors and uses for the same can be like those described in U.S. Pat. No. 9,008,757, entitled "Navigation System Including Optical and Non-optical Sensors," the entire disclosure of which is hereby incorporated by reference in its entirety.

The gyroscope sensors 60 may be 3-dimensional gyroscope sensors that measure angular velocities of the tracker 48. The gyroscope sensors 60 output readings indicative of the angular velocities relative to x-, y-, and z-axes of a gyroscope coordinate system. These measurements can then be converted to an angular velocity vector defined in radians/second.

The accelerometers 70 may be 3-axis accelerometers that measure acceleration along each of x-, y-, and z-axes of an accelerometer coordinate system.

The angular velocities measured by the gyroscope sensors 60 and the accelerations measured by the accelerometers 70 provide additional kinematic data for the navigation system 20 to further facilitate tracking of the tracker 48.

The gyroscope sensors 60 and the accelerometers 70 communicate with a tracker controller 62 located within the housing of the associated tracker 48 that facilitates transmission/reception of data to/from the navigation computer 26.

The tracker 48 additionally, or alternatively, may include sensors configured to perform tissue identification, e.g., when coupled to the anatomy. The generated data related to the identified tissue may be transmitted back to the localization device 34. Other examples of sensors that may be included with the tracker 48 include, but are not limited to, any one or more of camera/imaging/endoscopic sensors for visual object detection, biological sensors, bone density sensors, electromyography (EMG) sensors, nerve sensory sensors, ultrasonic sensors, electromagnetic sensors, environmental sensors (e.g., temperature, humidity, etc.), impedance, voltage, current sensors, pressure sensors, or the like. Data generated from any of the sensors is herein referred to as "sensor data" may be transmitted back to the localization device 34 from the tracker 48. The sensors may be utilized for navigation, anatomical registration, verification, calibration, instrument 22 control purposes, or the like. The sensor data transmitted by the tracker 48 may be generated by the tracker 48 itself or data otherwise received by the tracker 48 from an external source, e.g., a sensor external to and remotely communicating with the tracker 48.

As will be described below, the localization device 34 is configured to wirelessly receive the sensor data from the tracker 48 using one of the communication methods described herein. For example, the sensor data may be transmitted using RF communication such that the RF receiver 96 of the localization device 34 is configured to receive sensor data wirelessly from the RF transmitter 74 of the tracker 48.

With continued reference to FIG. 2, the navigation computer 26 includes a navigation processor 52. The camera unit 36 receives signals from the tracking sensors 40 and outputs to the navigation processor 52 signals relating to the position of the tracking markers 50 of the tracker 48 relative to the localization device 34. When the sensor data is used for navigation/tracking purposes, the RF receiver 94 receives data measured by the gyroscope sensors 60 and accelerometers 70, and outputs to the processor 52 signals relating to the measured angular velocities and/or accelerations. Based on the received IR and RF signals, navigation processor 52 generates data indicating the relative positions and orientations of the tracker 48 relative to the localization device 34.

The navigation processor 52 can include one or more processors to control operation of the navigation computer 26. The processors can be any type of microprocessor or multi-processor system. The term processor is not limited to a single processor.

Prior to the start of a surgical procedure, additional data may be loaded into the navigation processor 52. Based on the position and orientation of the tracker 48 and the previously loaded data, the navigation processor 52 may determine, for example, the position of the working end of the instrument 22 and the orientation of the instrument 22 relative to the tissue against which the working end is to be applied. In some embodiments, navigation processor 52 forwards these data to a manipulator controller 54. The manipulator controller 54 can then use the data to control the robotic manipulator 56 as described in U.S. patent application Ser. No. 13/958,834, entitled, "Navigation System for use with a Surgical Manipulator Operable in Manual or Semi-Autonomous Mode", the disclosure of which is hereby incorporated by reference.

The navigation processor 52 may include software modules such as a localization engine 100 and a coordinate transformer 102. These software modules 100, 102 collaborate to process the signals transmitted according to the first and second communication methods (e.g., IR and RF) to transform coordinate systems of the tracker 48, and consequently the object being tracked, into a coordinate system of the localization device 34 for purposes such as determining relative position of the instrument 22 working end to the surgical site (e.g., the bone of the patient). Other signals representative of this data can be forwarded to the manipulator controller 54 from the navigation processor 52 to control the manipulator 56 and corresponding movement of the instrument 22.

The navigation processor 52 may also process and generate image signals that indicate the relative position of the instrument 22 working end to the surgical site. These image signals may be transmitted to the displays 28, 29. The displays 28, 29, based on these signals, generate images that enable the surgeon and staff to view the position of the instrument 22 working end relative to the surgical site.

Techniques for combining IR data and data for tracking of the object can be like those described in U.S. Pat. No. 9,008,757, entitled "Navigation System Including Optical and Non-optical Sensors," the entire disclosure of which is hereby incorporated by reference in its entirety.

Examples of transformation techniques relating to coordinate systems of trackers 48, the object being tracked, and the localization device 34, can be like those described in U.S. Pat. No. 9,008,757, entitled "Navigation System Including Optical and Non-optical Sensors," the entire disclosure of which is hereby incorporated by reference in its entirety.

A. Hybrid Control for Implementing High-Bandwidth, Low Latency Communication

Incorporating sensors on the tracker 48 with a wireless tracking system requires a robust method of command and control to the wireless instruments that are being tracked by the localization device 34 as well as a high-speed, low latency method of reporting sensor measurements back to the localization device 34.

As described above, the localization device 34 and the tracker 48 communicate using the first and second communication methods. According to one advantage, the techniques herein provide high-speed, low latency communication by exploiting the first communication method for primary tracking and control and the second communication method for high-bandwidth data transmission. The system 20 is optimized to take advantage of the individual benefits of both communication methods to solve overall system issues that are not met by using either communication method on its own.

With reference to FIG. 3, techniques are described herein for implementing hybrid control for establishing high-bandwidth, low latency communication between the localization device 34 and the tracker 48. FIG. 3 is a method sequence diagram illustrating events/transmissions performed by the localization device 34 and/or the tracker 48 using the two different methods of communication. It should be understood that the sequence of steps shown in FIG. 3 are illustrative and are not limited specifically to the order shown, but rather may occur in a different order depending on a given situation.

As shown in FIG. 3, the localization device 34 and the tracker 48 are operable according to the first and second communication methods (demarcated by dashed lines). Such dual communication may be concurrent or non-concurrent. In this example, the localization device 34 is configured to utilize the first communication method to track the tracker 48. As shown at 200, the localization device 34 may employ communication on the first spectrum to obtain a position of the tracker 48, using any suitable tracking technique, such as those described above.

At 202, the localization device 34 further utilizes the first communication method to transmit a command signal to configure operation of the tracker 48 with respect to the second communication method. Such cross-communication configurations are represented generally at 204. As will be described below, these configurations dictate how the tracker 48 may behave with respect to the second communication method. Thus, the first communication method is utilized as the primary control and configuration channel for transmissions occurring with second communication method. In this specific example, the second communication method is utilized to provide a one-way secondary channel to transmit high bandwidth information from the tracker 48 to the localization device 34, as shown at 206. By using the second communication method in a uni-directional mode, the time required to switch directions is eliminated and greater bandwidth is achieved. In other words, control/configuration of the tracker 48 with respect to the second communication method is accomplished without requiring the localization device 34 to utilize the second communication method for control/configuration.

The methods described herein, however, are not limited to uni-directional transmission with the second communication method. Transmission with the second communication method between the localization device 34 and tracker 48 may be bi-directional, while still realizing the advantages provided by hybrid communication control.

FIG. 4 is a method sequence diagram illustrating events/transmissions performed by the localization device 34 and/or the tracker 48, wherein the first communication method is more specifically IR communication and the second communication method is more specifically RF communication. Although the techniques described with respect to FIG. 4 primarily focus on IR and RF communication for implementing hybrid control, the disclosure can be equivalently applied to microwave communication, which can substitute either IR or RF communication as a communication method. Again, the steps shown in FIG. 4 are not limited to the sequences shown.

With respect to the example of FIG. 4, the localization device 34 and the tracker 48 are operable according to the IR communication and RF communication. In this example, the localization device 34 is configured to utilize the IR communication to track the tracker 48, using, e.g. the IR tracking techniques described above. As shown at 300, the tracking sensors 40 of the localization device 34 obtain a position of the tracker 48 from the tracking markers 50 of the tracker 48 through the IR spectrum. At 302, IR signals received by the tracking sensors 40 of the localization device 34 are passed to the navigation computer 26 for object detection processing, as described.

For IR communication related to configuration/control, the localization device 34 utilizes the IR receiver 90 and the IR transmitter 98 and the tracker 48 utilizes the IR receiver 80 and the IR transmitter 51. Thus, the localization device 34 may further utilize IR communication to communicate IR control signals to the tracker 48.

At 304, the IR transmitter 98 of the localization device 34 may communicate the IR control signals 304 to the IR receiver 80 of the tracker 48 to manage operation of the tracker 48 with respect to IR communication. For example, using the IR control signals 304, the localization device 34 may initialize the tracker 48, configure the appropriate IR channel for the tracker 48, and/or control and command transmissions from the tracking markers 50 of the tracker 48 (as represented by loop 306). For instance, the IR control signal 304 may dictate sequential firing of IR emitters of the tracker 48, if present.

The tracker 48 may transmit IR signals from the IR transmitter 51 to the IR receiver 90 of the localization device 34 for certain communication/control purposes. Thus, the tracker 48 is configured to utilize the IR transmitter 51 for both communication as well as tracking. With continued reference to FIG. 4, the localization device 34 may also use the IR control signal 304 to manage IR transmissions from the IR transmitter 51 of the tracker 48 (as represented by loop 307). For example, IR communication from the tracker 48 may include operational status data of the tracker 48, identification data, calibration data, or any operational parameters of the tracker 48 that may be utilized, e.g., for synchronization or coordination with the localization device 34. Thus, at 305, the IR transmitter 51 of the tracker 48 sends an IR control signal back to the IR receiver 90 of the localization device 34.

In the example of FIG. 4, IR communication between the tracker 48 and localization device 34 for communication/control occurs on a first IR channel (IR channel 1) operating on a first frequency or frequency range. On the other hand, signal transmission for tracking the tracker 48 occurs on a second IR channel (IR Channel 2) operating on a second frequency or frequency range that is different than IR Channel 1. Thus, in one embodiment, the IR channel used for localization and the IR channel used for control/communication are different. These IR channels may be on different frequencies of the IR spectrum to avoid signal interference and to provide a more robust communication link. Alternatively, IR communication and tracking may occur on the same IR channel by employing, for example, timing schemes for avoiding signal interference.

As described above, IR communication has been utilized by the localization device 34 for two purposes, namely, localization and communication/control of the tracker 48 with respect to IR communication. However, in accordance with the hybrid-control techniques described herein, the localization device 34 may further utilize IR communication for a third purpose, i.e., communication/control of the tracker 48 with respect to RF communication.

As such, at 308, the localization device 34 utilizes IR communication to control/configure the tracker 48 with respect RF communication. The IR transmitter 98 of the localization device 34 is configured to transmit a control signal 308 to the IR receiver 80 of the tracker for configuring an operating parameter of the tracker 48 with respect to the RF communication. In general, these operating parameters dictate how the tracker 48 may behave with respect to RF communication.

In the example of FIG. 4, the localization device 34 transmits this control signal 308 for RF communication using IR channel 1 to avoid interference with localization signals on IR channel 2. However, it is possible to transmit the control signal 308 for RF communication using any IR channel, including IR channel 1, as described above.

Examples of some operating parameters of the tracker 48 that can be configured with the RF control signal 308 are represented at 310, 312, 313 and 314. Operating parameters of the tracker 48 with respect to RF communication other than those described herein are possible and contemplated.

For example, the operating parameter at 310 manages transmissions from the RF transmitter 74 of the tracker 48 to the RF receiver 96 of the localization device 34. RF timing parameters that may be managed through IR communication include, but are not limited to, transmission time, sequence, duration, interval, start and end times, etc. Such timing parameters may be controlled to synchronize RF communications between the tracker 48 and the localization device 34.

The operating parameter 310 manages RF transmission for sensor data being transmitted by the tracker 48. For example, the sensor data transmitted by the tracker 48 may be any data needful of a high bandwidth and low latency wireless link. In this example, the operating parameter 310 may manage when to transmit sensor data, how long to transmit sensor data, and what/how much sensor data to transmit from the tracker 48. Additionally or alternatively, data transmitted by the tracker 48 using RF communication may include, but is not limited to, non-sensor data, such as status data, error data, configuration data, identification data, etc.

At 316, the RF transmitter 74 of the tracker 48 transmits the data to the RF receiver 96 of the localization device 34. In the example where the sensor data transmitted is inertial data, the RF receiver 94 receives the inertial data and outputs signals to the processor 52 relating to the measured angular velocities and/or accelerations. Based on the received IR signals (at 300, 302) and RF signals (at 316, 318), navigation processor 52 generates data indicating the relative positions and orientations of the tracker 48 relative to the localization device 34 for tracking the object.

In FIG. 4, RF communication is utilized in a uni-directional fashion to transmit high bandwidth information from the tracker 48 to the localization device 34. By using RF communication uni-directionally, the time required for switching RF transmission directions between the RF tracker 48 and the localization device 34 is eliminated and greater bandwidth is achieved for RF communications. In other words, control/configuration of the tracker 48 with respect to the RF communication is accomplished without requiring the localization device 34 to utilize the RF communication for control/configuration. The methods described herein, however, are not limited to uni-directional RF transmission, as shown in FIG. 4. Instead, RF transmission between the localization device 34 and the tracker 48 may be bi-directional, while still realizing the advantages provided by hybrid communication control. For instance, RF communication direction may be switched (i.e., so that the localization device 34 transmits to the tracker 48) when the localization device 34 knows that the tracker 48 is not transmitting data. Thus, high bandwidth and low latency communication on the RF spectrum can be realized bi-directionally as well.

Another operating parameter that can be managed with the control signal 308 is a parameter, at 312, that coordinates RF transmission from the tracker 48 and operation of the tracking markers 50 of the tracker 48. This operating parameter 312 can coordinate wireless transmission of the sensor data from the RF transmitter 74 of the tracker and activation of the active tracking markers 50. For example, the relative sampling rates of the gyroscope sensors 60 and accelerometers 70 and the tracking sensors 40 of the localization device 34 may be established or timed so that for each optical measurement of position there is a corresponding non-optical measurement of angular velocity or acceleration. By coordinating transmissions, the localization device 34 is configured to receive IR and RF signals from the tracker 48 at known or predictable times to increase tracking accuracy of the object. Return of sensor data from the tracker 48 may be synchronized by IR frame commands.

The operating parameter at 313 coordinates transmissions from the RF transmitter 74 and the IR transmitter 51 of the tracker 48. For example, IR tracker communication/control signals (305) transmitted from the tracker 48 may need to be coordinated with respect to the timing of sensor data transmitted by the RF transmitter 74. For example, the localization device 34 may ping the tracker 48 to send coordinated RF and IR signals for confirming proper RF and IR link.

Other operating parameters of the tracker 48 relative to RF communication that can be controlled by the control signal 308 include RF channel frequency and RF transmission power, as shown at 314.

As described above, the RF spectrum comprises a plurality of RF channels with each RF channel operating on a different channel frequency. To establish RF communication with the localization device 34, the tracker 48 should be tuned or otherwise configured to operate on the RF channel specified by the localization device 34. When several trackers 48 are present, each separate tracker 48 may operate on a different RF channel specified by the localization device 34. Alternatively, more than one tracker 48 may operate on the same RF channel, and the respective RF transmitter 74 of each tracker 48 can be coordinated to transmit RF signals according to a sequential time-slicing scheme coordinated by the localization device 34. For instance, the time-slicing scheme may set a repeating period of time, and each tracker 48 sequentially transmits, in turn, during each period. Each tracker 48 may transmit a specified number of times, or for a specified duration during each time slice of the period of time.

By sending the control signal 308, the localization device 34 utilizes IR communication to inform the tracker 48 to select, or otherwise configure the tracker 48 to operate on, the RF channel specified by the localization device 34. As represented at 314, the RF transmitter 74 of the tracker 48 then operates at the frequency for the specified RF channel. The RF channel may continue to change depending on, for example, the activation/deactivation of various trackers 48, etc.

The control signal 308 may be sent to modify the RF transmission power of the tracker 48 at 314. More specifically, the operating parameter specifies transmission power of the RF transmitter 74 of the tracker 48. Transmission power may be modified for various purposes, such as to accommodate changes in RF channel frequency, to increase RF signal strength of the tracker 48, e.g., when interference is present, to increase battery life of the tracker 48, etc. Other examples of RF transmission parameters that may be modified using the control signal 308 include, but are not limited to, any variation of effective radiated power, nominal power, signal strength, attenuation, sensitivity, antenna gain, impedance, radiation pattern, and the like. Operating parameters of the tracker 48 with respect to RF communication other than those described herein are possible and fully contemplated.

While the various operating parameters 310, 312, 313, 314 described above have been discussed in relation to modifying operation of the tracker 48 with respect to RF communication, it should be understood that such operating parameters may control operation of the tracker 48 with respect to a different method of communication if the system 20 is so configured. For instance, if the second method of communication is microwave communication, the operating parameters may control microwave transmission, microwave frequency, microwave channel, etc.

Furthermore, the system 20 may employ any number of different communication methods greater than two. For instance, the system 20 may employ IR communication, RF communication and microwave communication. The purpose of each communication method can be different from the others, or partially the same as others. For instance, IR communication may be utilized for localization and configuration/control while RF and microwave communication are utilized for high-bandwidth data transmission. Alternatively, IR and RF communication may be utilized for localization and configuration/control while microwave communication is utilized for high-bandwidth data transmission.

III. Diversity Techniques

Figure 5A:
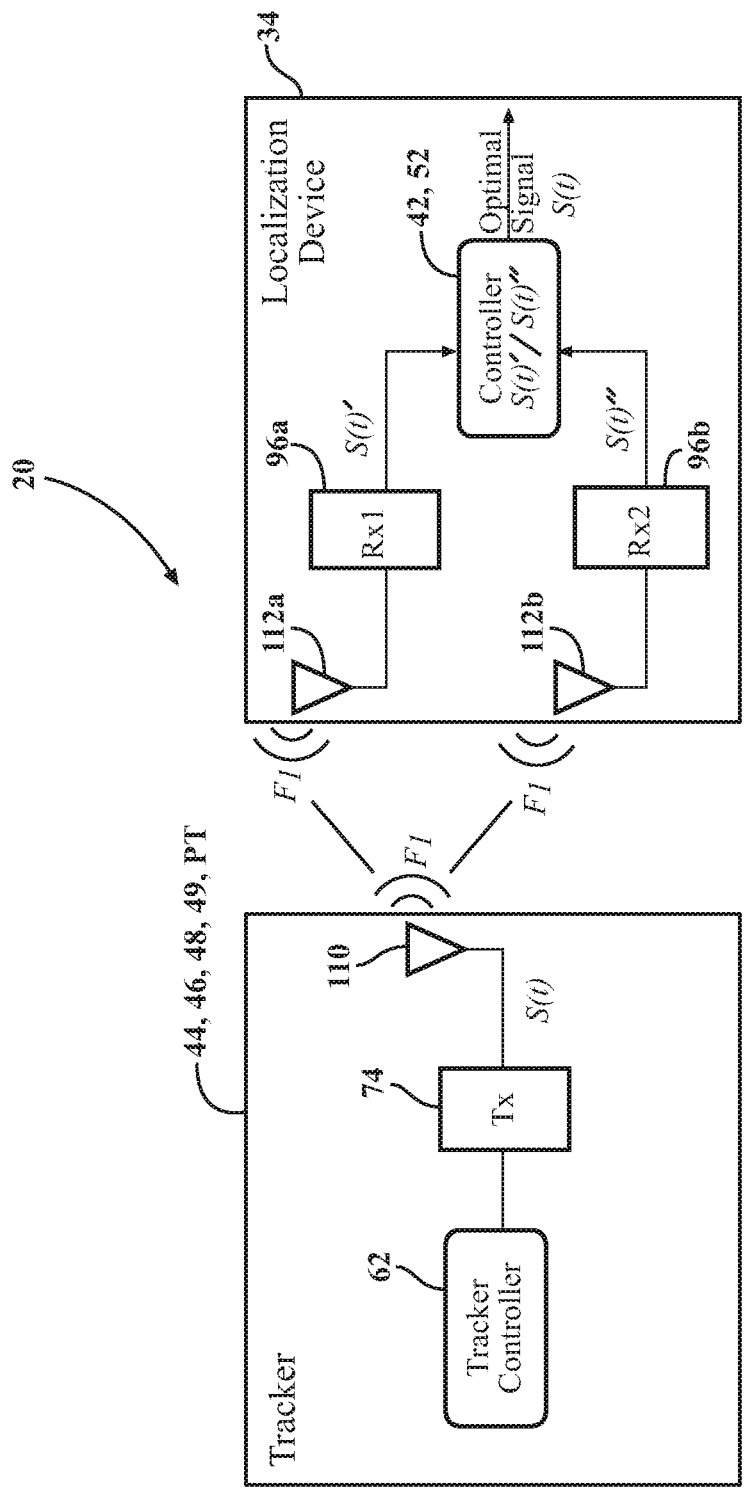
FIG. 5A is a block diagram of the localization device and the tracker and components thereof according to one example wherein the localization device is implementing spatial diversity techniques for receiving RF transmissions from the tracker.
Figure 5B:
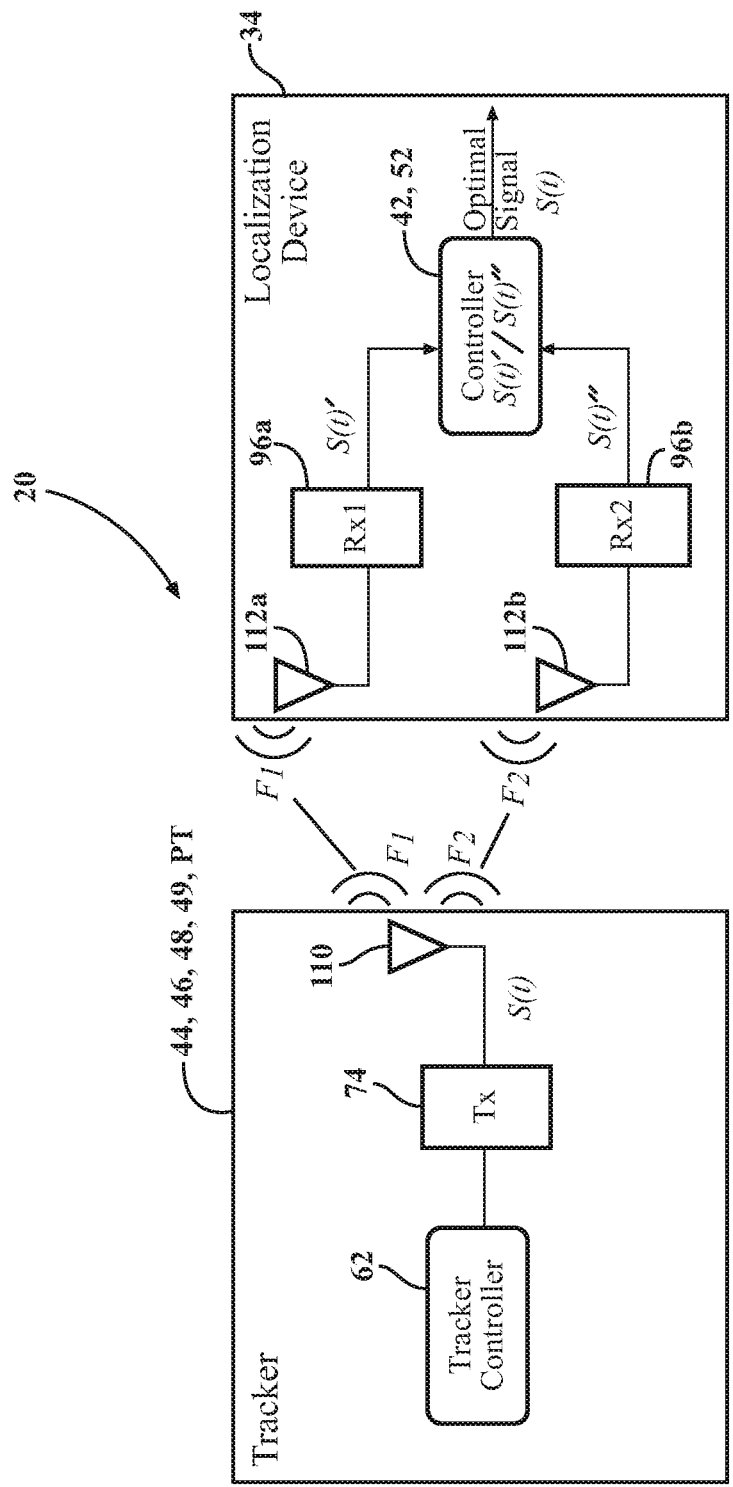
FIG. 5B is a block diagram of FIG. 5A wherein the localization device is further implementing spectrum diversity techniques for receiving RF transmissions from the tracker.

With reference to FIGS. 5A and 5B, the system 20 may further implement features for maximizing robustness of communication using diversity techniques. Diversity techniques include, but are not limited to antenna diversity, spectrum diversity, transmit/receive diversity, time diversity, spatial diversity, frequency diversity, pattern diversity, or any combination thereof. Such techniques are employed to improve the quality and reliability of the wireless link between the tracker 48 and the localization device 34.

In one example, diversity is utilized for the second communication method, rather than the first communication method used for localization. In another example, diversity is utilized for both the first and second communication methods.

Continuing with the example of FIG. 4 utilizing hybrid IR/RF communication, the system 20 may employ antenna (spatial) diversity for RF communication. One example of the antenna diversity scheme is illustrated in FIG. 5A. Antenna diversity may involve utilizing more than one RF receiver 96 and/or antenna 112 at the localization device 34 to improve the RF wireless link. Alternatively, one RF receiver 96 and one antenna 112 may be utilized with a time-slicing scheme, as described above.

In the example of FIG. 5A, the localization device 34 is equipped with two RF receivers 96a, 96b, each having a dedicated antenna 112a, 112b, respectively. In other examples, two antennas 112a, 112b may be utilized with a common RF receiver 96, rather than two dedicated RF receivers 96a, 96b. The antennas 112a, 112b are placed at different locations relative to one another such that each antenna 112a, 112b can receive RF signals from the tracker 48 according to a different transmission path. For instance, one antenna 112a may be placed on the camera unit 36 while the other antenna 112b is placed elsewhere on the computer cart assembly 24 or even the manipulator cart 59. The camera controller 42, and/or the navigation processor (controller) 52 are configured to control and operate the RF receivers 96a, 96b for implementing diversity techniques.

In this example, the tracker controller 62 instructs the RF transmitter 74 of the tracker 48 to transmit an RF signal S(t) for any purpose, such as for transmitting tracker sensor data, or more specifically inertial data, as described above. The RF signal S(t) is transmitted at a first frequency F1. The RF signal S(t) may be transmitted through a single RF channel. The RF signal S(t) propagates through the air at frequency F1 and reaches each of the antennas 112a, 112b at the localization device 34 according to different transmission paths.

Each of the antennas 112a, 112b is configured for the same RF channel for receiving the RF signal S(t) at the first frequency F1. Each of the RF receivers 96a, 96b receive the RF signal, i.e., S(t)' and S(t)" differently because of the different transmission paths and spatial diversity positioning of the antennas 112a, 112b. One or more of the controllers 42, 52 processes the RF signals S(t)' and S(t)" and determines which of the RF signals S(t)' and S(t)" are most optimal for downstream tracking determinations. One or more of the controllers 42, 52 then selects the optimal one of the RF signals S(t)' and S(t)" that is most representative of the originally transmitted RF signal S(t), and disregards the other. The optimal signal S(t) can be processed by the navigation processor 52 to generate data indicating the relative positions and orientations of the tracker 48 relative to the localization device 34 for tracking the object. Such antenna diversity techniques may be utilized with any communication method described herein.

The hybrid control techniques described above may be utilized to control the tracker 48 to implement spatial diversity. For instance, the localization device 34 may command the tracker 48 using IR communication to repeatedly transmit data according to the first frequency F1 on the RF channel. The operating parameter in this instance may specify the first frequency F1 for the RF transmitter 74 of the tracker 48 as well as how often to transmit the RF signal at the first frequency F1. Any of the other operating parameters 310, 312, 313, 314 relating to transmission timing, power, coordination, etc., may be additionally utilized to implement spatial diversity.

In another technique, as illustrated in FIG. 5B, the system 20 exploits the antenna diversity scheme of FIG. 5A by further utilizing spectrum diversity. In this example, the tracker controller 62 instructs the RF transmitter 74 of the tracker 48 to transmit an RF signal S(t), as described above. However, the RF signal S(t) is transmitted at a first frequency F1 as well as a second frequency F2 that is different from the first frequency F1. Despite the two different frequencies, F1, F2, the RF signal S(t) carries the same data for transmission. There may be short time delay between transmissions the RF signal S(t) at the two frequencies F1, F2. Alternatively, the tracker 48 may simultaneously transmit these signals. The RF signal S(t) at the two frequencies F1, F2 may be transmitted according to two different RF channels. Antenna 112a and receiver 96a may be configured for one RF channel and antenna 112b and receiver 96b may be configured for the second RF channel The RF signals S(t) propagate through the air and the antenna 112a receives the RF signal S(t) at frequency F1 and the antenna 112b receives the RF signal S(t) at frequency F2.

Each of the RF receivers 96a, 96b receive a different version of the RF signal, i.e., S(t)' and S(t)" at the respective frequencies F1, F2. One or more of the controllers 42, 52 processes the RF signals S(t)' and S(t)" and determines which of the RF signals S(t)' and S(t)" are most optimal for downstream processing. One or more of the controllers 42, 52 then selects the optimal one of the RF signals S(t)' and S(t)" that is most representative of the originally transmitted RF signal S(t) and disregards the other. The optimal signal S(t) can be processed by the navigation processor 52 to generate data indicating the relative positions and orientations of the tracker 48 relative to the localization device 34 for tracking the object.

Although two receivers 96a, 96b and two antennas 112a, 112b are used in this example, spectrum diversity may instead be implemented using one RF receiver 96 and one antenna 112 utilizing a sequential time-slicing scheme, as described above. Such spectrum diversity techniques may be utilized with any communication method described herein.

The hybrid control techniques described above may be utilized to control the tracker 48 to implement spectrum diversity. For instance, the localization device 34 may command the tracker 48 using IR communication to transmit data according to the first frequency F1 on the first RF channel and according to the second frequency F2 on the second RF channel. The operating parameter in this instance specifies the first and second frequencies F1, F2, for the RF transmitter 74 of the tracker 48 and manages RF transmitter 74 switching between the first and second frequencies F1, F2 to implement spectrum diversity. Any of the other operating parameters 310, 312, 313, 314 relating to transmission timing, power, coordination, etc., may be additionally utilized to implement spectrum diversity.

In yet another technique, one or more of the controllers 42, 52 is configured to operate one of the RF receivers 96a to receive data wirelessly from the RF transmitter 74 of the tracker 48 and to operate the other one of the RF receivers 96b to detect availability of, or otherwise evaluate, one or more other RF channels on the RF spectrum. Data can be received on one RF channel concurrently while other RF channels are detected or evaluated. If one of the RF channels is occupied, or otherwise exhibits interference above a specified threshold, the localization device 34 can select other RF channels. Furthermore, if the RF channel receiving the data is less optimal than another RF channel because of interference, for example, the localization device 34 can command switching of RF transmission to the more optimal RF channel The RF channel that previously was receiving data can then be utilized to detect and evaluate other RF channels, and so on. Such switching can be implemented by using the command signal 308 transmitted from the localization device 34 on the IR spectrum.

In so doing, rapid channel switching of trackers 48 can be performed immediately and without delay caused by data reception. Any number of antennas 112 and receivers 96 can be employed for these various methods. For instance, this technique can be implemented with a single RF receiver 96 and a single antenna 112 with sequential time slicing. Additionally, spatial or spectrum diversity can be implemented by certain receivers 96 while other receivers search for available channels. These techniques can utilized with any one or more of the communication methods described herein, or equivalents thereof.

IV. Different Modulation Methods

The examples above focus on high bandwidth, low latency communication techniques for the navigation system 20 by utilizing communication according to the first spectrum for tracking and configuration control (managing the operating parameter) of the tracker while using the second spectrum for transmitting the tracker sensor data. It is possible to achieve the technical solutions described above for the navigation system 20 by utilizing communication according to an additional or alternative technique, both involving different first and second methods of modulation. These techniques are described in subsections A and B below.

The systems, methods and techniques described herein address issues of the prior art by providing high-speed, low latency and deterministic communication between the localization device and tracker, thereby improving system accuracy and stability. The techniques utilize two different modulation methods for wirelessly communicating with the tracker without requiring a cable physically connected between the tracker and the localization device. In turn, the surgical workspace is less cluttered by cables.

Furthermore, by utilizing the first modulation method to manage an operating parameter of the tracker, the techniques described herein free-up bandwidth on the communication spectrum. Freeing up bandwidth enables high-speed wireless transmission of data between the localization device and the tracker. Such data can be, for example, sensor data, which often requires much bandwidth.

In turn, the systems, methods and techniques described herein exploit the advantages of different modulation methods to provide robust command and control to wireless trackers that are being tracked by the localization device as well as a high-speed, low latency method of reporting data back the localization device.

In one example, the first modulation method comprises one of amplitude modulation, frequency modulation, phase modulation, pulse width modulation, pulse position modulation, pulse duration modulation, trellis-coded modulation, and on-off keying modulation. Since the second modulation is different from the first modulation method, the second modulation method comprises a different one of amplitude modulation, frequency modulation, phase modulation, pulse width modulation, pulse position modulation, pulse duration modulation, trellis-coded modulation, and on-off keying modulation. The navigation system 20 can utilize variations, or species, of the modulation methods described herein as well as modulation methods that may not expressly be recited herein.

Communication according to the first modulation method comprises modulating a first carrier signal, and communication according the second modulation method comprises modulating a second carrier signal. The carrier signal is a waveform that is modulated according to the methods described herein for conveying data. In one example, a frequency of the first carrier signal is different from a frequency of the second carrier signal. For instance, the second carrier frequency may be 10 times, 100 times, 1000 times the first carrier frequency. As such, the second modulation method is capable transmitting higher bandwidth as compared with the first communication method.

When IR communication is utilized, for example, the frequency of the first carrier signal may be 1 MHz and the frequency of the second carrier signal may be 10 MHz. When RF communication is utilized, for example, the frequency of the first carrier signal may be 1 GHz and the frequency of the second carrier signal may be 10 GHz. The carrier frequencies described herein are not limiting and other carrier frequencies besides those listed herein may be utilized.

The navigation system 20 can employ any number of different modulation methods greater than two. For example, the navigation system 20 can employ four, six or eight different modulation methods.

Any of the hardware or capabilities of the navigation system 20 described above in the previous sections can be utilized for this alternative technique. For simplicity, the descriptions of such hardware and capabilities are not repeated, but should be considered fully incorporated herein.

A. Different Modulation Methods Utilized with Different Spectrums of Communication Expanding on the dual spectrum techniques described above, this example further utilizes a first modulation method for communication on the first spectrum while utilizing a second modulation method for communication on the second spectrum.

For example, the navigation system 20 can utilize communication according to the different spectrums (e.g., IR and RF), as described above, however, the navigation system 20 can further utilize the first modulation method for tracking and configuration control (managing the operating parameter) of the tracker according to communication on the first spectrum, while using a second modulation method for transmitting the tracker sensor data according to communication on the second spectrum.

For instance, with reference back to FIG. 3, the localization device 34 and the tracker 48 are operable according to the first and second communication spectrums (demarcated by dashed lines). As described above, and as shown at 200, the localization device 34 may employ communication on the first spectrum to obtain a position of the tracker 48 and at 202, the localization device 34 further utilizes the first communication spectrum to transmit a command signal to configure operation of the tracker 48. As an added feature, steps 200 and 202 occur not only the first spectrum, but also by utilizing the first modulation method. One the other hand, at 206, the tracker transmits high bandwidth information to the localization device 34 using communication according to communication on the second spectrum. As an added feature, step 206 occurs not only the second spectrum, but also by utilizing a second modulation method that is different from the first modulation method.

B. Different Modulation Methods Utilized with One Spectrum of Communication

Figure 6:
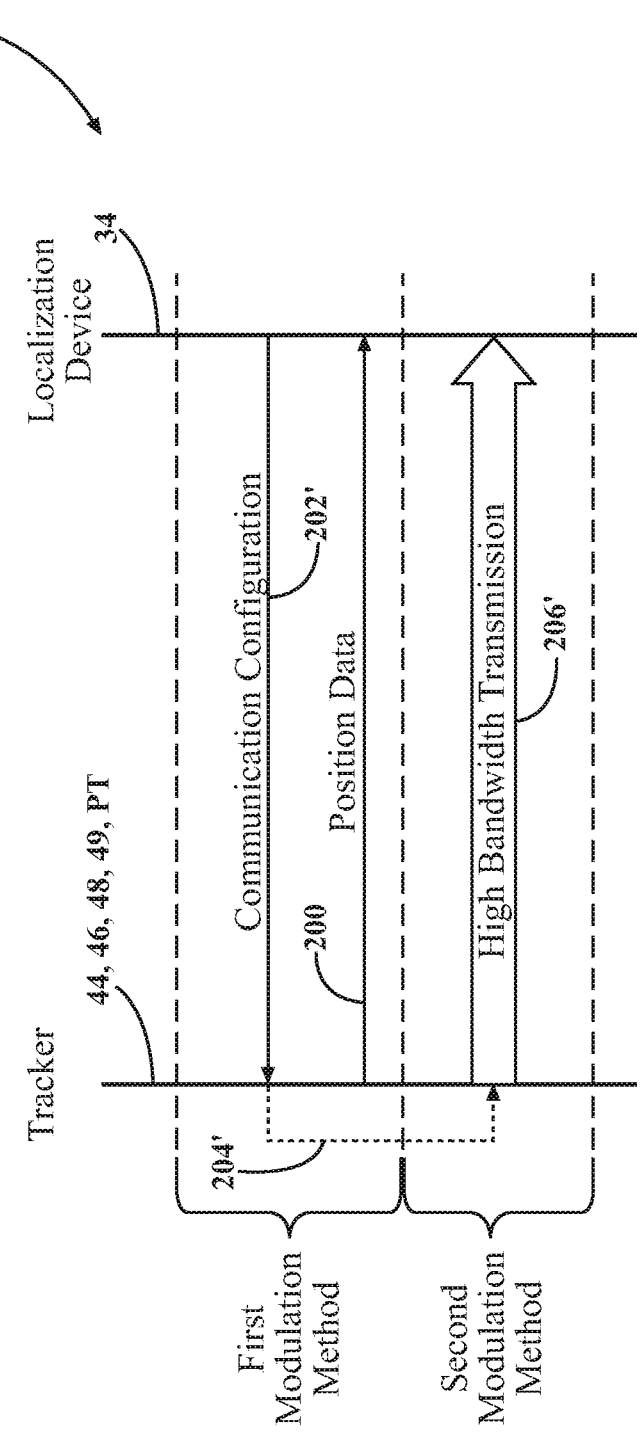

As an alternative to the techniques described in the previous sections, and with reference to FIG. 6, the navigation system 20 can utilize communication according to one spectrum (e.g., IR or RF), instead of two different spectrums. With the one spectrum, high bandwidth, low latency hybrid communication can be implemented by utilizing different modulation methods. Specifically, the navigation system 20 can utilize a first modulation method for tracking and configuration control (managing the operating parameter) of the tracker while using a second modulation method for transmitting the tracker sensor data. The first and second modulation methods are different from one another but are employed on the same spectrum of communication.

For example, with reference to FIG. 6, the localization device 34 and the tracker 48 communicate according to one communication spectrum. However, in this example, the localization device 34 employs communication according to a first modulation method to obtain a position of the tracker 48 (step 200) and to transmit a command signal to configure operation of the tracker 48 (at 202', 204'). One the other hand, at 206', the tracker transmits high bandwidth information to the localization device 34 using communication on the same spectrum, but by employing a second modulation method.

According to one example of implementing this alternative technique, and with reference to FIG. 7, the spectrum is IR communication. The navigation system 20 comprises the tracker 44, 46, 48, 49, PT and the localization device 34. The tracker 44, 46, 48, 49, PT includes the IR transmitter 51, the IR receiver 80, one or more tracking markers 50, and one or more sensors configured to generate sensor data. In one example, the sensors are one or more gyroscope sensors 60 and/or one or more accelerometers 70 configured to generate inertial data. The localization device 34 comprises the IR receiver 90, the IR transmitter 98, and one or more tracking sensors 40. The localization device 34 is configured to utilize IR communication according to the different first and second modulation methods, as shown.

Utilizing IR communication according to the first modulation method, the localization device 34 detects (at 300) a position of the one or more tracking markers 50 of the tracker 44, 46, 48, 49, PT with the one or more tracking sensors 40. Utilizing IR communication according to the first modulation method, the localization device 34 also communicates (at 308'), using the IR transmitter 98, with the IR receiver 80 of the tracker to manage an operating parameter of the tracker with respect to IR communication. At 304, the IR transmitter 98 of the localization device 34 may communicate the IR control signals 304 to the IR receiver 80 of the tracker 48 to manage operation of the tracker 48 with respect to IR communication. Step 304 occurs on the IR spectrum using the first modulation method. Example functionality of the IR control signals are the same as those described in the previous sections. At 305, the IR transmitter 51 of the tracker 48 can send an IR control signal back to the IR receiver 90 of the localization device 34 on the IR spectrum using the first modulation method.

Utilizing IR communication according to the second modulation method, the localization device 34 is configured to wirelessly receive (at 316'), with the IR receiver 90, the inertial data generated by the tracker and transmitted by the IR transmitter 51 of the tracker in accordance with the managed operating parameter of the tracker.

According to another example of implementing this technique, the spectrum is RF communication. For example, for RF communication, the tracker can comprise the RF transmitter 74 and an RF receiver, and the RF receiver and the localization device 34 can comprise the RF receiver 96 and an RF transmitter. The tracking sensors 40 can be modified as RF tracking sensors 40. Alternatively, the RF receiver 96 itself can operate as a tracking sensor to track RF tracking markers on the tracker. The localization device 34 may be configured to utilize RF communication according to the first modulation method and the second modulation method. By utilizing RF communication according to the first modulation method, the localization device 34 is configured to detect a position of the one or more RF tracking markers of the tracker with the one or more tracking sensors 40. By utilizing RF communication according to the first modulation method, the localization device 34 is further configured to communicate, using the RF transmitter, with the RF receiver of the tracker to manage an operating parameter of the tracker with respect to RF communication. By utilizing RF communication according to the second modulation method, the localization device 34 is configured to wirelessly receive, with the RF receiver 96, the inertial data generated by the tracker and transmitted by the RF transmitter 74 of the tracker in accordance with the managed operating parameter of the tracker.

Although IR and RF examples are described above, the different modulation methods can be utilized for any other spectrum of communication described herein.

In some instances, the modulation methods can be reversed during operation of the navigation system 20. For example, at a first stage, the navigation system 20 can utilize the first modulation method for tracking and configuration control (managing the operating parameter) of the tracker while using the second modulation method for transmitting the tracker sensor data. At a second stage, the navigation system 20 can utilize the second modulation method for tracking and configuration control (managing the operating parameter) of the tracker while using the first modulation method for transmitting the tracker sensor data.

In yet another example, the different pairs of modulation methods can be employed at different stages. For example, at a first stage, the navigation system 20 can utilize the first modulation method for tracking and configuration control (managing the operating parameter) of the tracker while using the second modulation method for transmitting the tracker sensor data. At a second stage, the navigation system 20 can utilize a third modulation method for tracking and configuration control (managing the operating parameter) of the tracker while using a fourth modulation method for transmitting the tracker sensor data. The third and fourth modulation methods can be different from the first and second modulation methods. Examples of such variations/selections of modulation methods are possible other than those expressly recited herein.

The modulation methods can be preconfigured into the tracker and localization system 34, e.g., based on optimal performance given the hardware and operational considerations of the navigation system 20. In other examples, an operator of the navigation system 20 can select and manipulate the modulation methods by using software on the navigation system 20 display 29. In other example, the modulation methods can be dynamically changed during operation of the navigation system 20. For example, the navigation system 20 can detect performance metrics according to a modulation method to assess whether a different modulation method would perform more optimally. In such instances, the localization device 34 can treat selection of the modulation method as one of the operating parameters. The localization device 34 can internally configure its transmitter/receiver for a selected modulation method and utilize the transmitter to communicate with the receiver of the tracker to configure communication according to the selected modulation method so that coding/decoding of data will be properly synchronized.

When using different modulation modes on the same spectrum, the operating parameter that is managed can be the same as of the operating parameters described in the previous sections, e.g., for managing transmission power, transmission channel, transmission frequency, transmission timing, coordination of transmission/reception for tracking, etc. However, since one spectrum may be utilized instead of two, the operating parameter in this technique may be specific to the one spectrum. For example, when IR communication is used, the operating parameter can specify IR transmission timing, IR channel selection, IR channel frequency, IR transmission power, or coordination of IR transmission and IR reception of the tracker. Similarly, when RF communication is used, the operating parameter can specify RF transmission timing, RF channel selection, RF channel frequency, RF transmission power, or coordination of RF transmission and RF reception of the tracker.

In addition, the operating parameter can also include selection of a modulation method, selection of decoding/encoding schemes, or other behavior of the tracker to enable or coordinate communication according to the different modulation methods. All other description regarding operating parameters in the sections described above can be fully applied to the embodiment of this section, and are not repeated for simplicity in description. Hence, such descriptions should be considered fully incorporated in this section by reference.

Furthermore, the diversity techniques described in the section III can also be applied to this alternative technique. For example, for IR communication, the localization device 34 may further comprise a second IR receiver 90' and a controller for operating the IR receivers 90, 90'. The controller can operate the IR receivers using spatial diversity such that both IR receivers receive data wirelessly from the IR transmitter of the tracker. The controller can operate one of the IR receivers to receive data wirelessly from the IR transmitter of the tracker and operate the other one of the IR receivers for detecting availability of one or more IR channels on the IR spectrum.

The controller can further operate the IR receivers 90, 90' of the localization device 34 using spectrum diversity such that one of the IR receivers receives data wirelessly from the IR transmitter of the tracker through a first RF channel at a first frequency on the IR spectrum and such that the other one of the IR receivers receives data wirelessly from the IR transmitter of the tracker through a second IR channel at a second frequency that is different from the first frequency on the IR spectrum. The operating parameter can specify the first and second frequencies for the IR transmitter of the tracker and manages switching between the first and second frequencies for the IR transmitter of the tracker to implement spectrum diversity. The description in the preceding paragraphs can be applied fully with respect to RF communication, as described similar to the section III above.

It is an object of the intended claims to cover all such modifications and variations that come within the true spirit and scope of this invention. Furthermore, the embodiments described above are related to medical applications, but the inventions described herein are also applicable to other applications such as industrial, aerospace, defense, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A navigation system for tracking an object, the navigation system comprising:
   a tracker configured to couple to the object and comprising one or more optical tracking elements and a tracker transmitter; and
   a localization device configured to track the tracker;
   wherein the tracker and the localization device are configured to wirelessly communicate using an optical communication method and to wirelessly communicate using a non-optical communication method; and
   wherein the localization device is configured to utilize the optical communication method to track the one or more optical tracking elements of the tracker and to utilize the optical communication method to manage an operating parameter of the tracker with respect to the non-optical communication method;
   wherein the operating parameter specifies one or more of: a channel frequency for the tracker transmitter, and a transmission power of the tracker transmitter.

2. The navigation system of claim 1, wherein the localization device comprises one or more tracking sensors configured to detect a position of the one or more optical tracking elements for tracking the tracker using the optical communication method.

3. The navigation system of claim 1, wherein:
   the localization device comprises a localization device transmitter;
   the tracker further comprises a tracker receiver;
   the localization device transmitter and the tracker receiver communicate using the optical communication method; and
   wherein the localization device is configured to utilize the localization device transmitter to communicate with the tracker receiver to manage the operating parameter of the tracker with respect to the non-optical communication method.

4. The navigation system of claim 3, wherein the localization device is further configured to utilize the localization device transmitter to communicate with the tracker receiver using the optical communication method to manage an operating parameter of the tracker with respect to the optical communication method.

5. The navigation system of claim 1, wherein:
the localization device comprises one or more tracking sensors configured to detect a position of the one or more optical tracking elements for tracking the tracker by utilizing a first channel; and
the localization device comprises a localization device transmitter and the tracker comprises a tracker receiver and wherein the localization device utilizes the localization device transmitter to communicate with the tracker receiver to manage the operating parameter of the tracker with respect to the non-optical communication method by utilizing a second channel being different from the first channel.

6. The navigation system of claim 1, wherein the localization device comprises a localization device receiver, and wherein the tracker transmitter and the localization device receiver are configured to communicate using at least the non-optical communication method.

7. The navigation system of claim 1, wherein the localization device comprises a localization device receiver and with the tracker transmitter and the localization device receiver being configured to communicate using the non-optical communication method, and wherein the tracker comprises one or more inertial sensors configured to generate inertial data, and wherein the localization device receiver is configured to wirelessly receive the generated inertial data from the tracker transmitter using the non-optical communication method.

8. The navigation system of claim 7, wherein the operating parameter manages timing of wireless transmission of the generated inertial data from the tracker transmitter.

9. The navigation system of claim 7, wherein the localization device comprises one or more tracking sensors configured to detect a position of the one or more optical tracking elements for tracking the tracker using the optical communication method, and wherein the operating parameter coordinates both timing of wireless transmission of the generated inertial data from the tracker transmitter and operation of the one or more optical tracking elements of the tracker.

10. The navigation system of claim 7, wherein the operating parameter specifies first and second frequencies for the tracker transmitter and manages switching between the first and second frequencies for the tracker transmitter to implement spectrum diversity.

11. The navigation system of claim 1, wherein:
the optical communication method is further defined as infrared (IR) communication; and
the non-optical communication method is further defined as microwave communication or RF communication.

12. A method of operating a navigation system configured to track an object, the navigation system comprising a tracker configured to couple to the object and including one or more optical tracking elements and a tracker transmitter, and a localization device configured to track the tracker, wherein the tracker and the localization device are configured to wirelessly communicate using an optical communication method and to wirelessly communicate using a non-optical communication method, the method comprising the steps of:
utilizing, with the localization device, the optical communication method to track the one or more optical tracking elements of the tracker; and
utilizing, with the localization device, the optical communication method to manage an operating parameter of the tracker with respect to the non-optical communication method;
wherein the operating parameter specifies one or more of: a channel frequency for the tracker transmitter, and a transmission power of the tracker transmitter.

13. The method of claim 12, wherein the localization device comprises one or more tracking sensors, and further comprising:
detecting, with the one or more tracking sensors of the localization device, a position of the one or more optical tracking elements for tracking the tracker using the optical communication method.

14. The method of claim 12, wherein the localization device comprises a localization device transmitter and the tracker comprises a tracker receiver with the localization device transmitter and tracker receiver being configured to communicate using the optical communication method, and further comprising:
communicating, utilizing the localization device transmitter, with the tracker receiver to manage the operating parameter of the tracker with respect to the non-optical communication method.

15. The method of claim 14, further comprising:
communicating, utilizing the localization device transmitter, with the tracker receiver to manage an operating parameter of the tracker with respect to the optical communication method.

16. The method of claim 12, the localization device comprises one or more tracking sensors, and wherein the localization device comprises a localization device transmitter and the tracker comprises a tracker receiver, and further comprising:
detecting, with the one or more tracking sensors of the localization device, a position of the one or more optical tracking elements for tracking the tracker by utilizing a first channel; and
communicating, utilizing the localization device transmitter and the optical communication method, with the tracker receiver to manage the operating parameter of the tracker with respect to the non-optical communication method by utilizing a second channel being different from the first channel.

17. The method of claim 12, wherein the localization device comprises a localization device receiver and with the tracker transmitter and the localization device receiver being configured to communicate using the non-optical communication method.

18. The method of claim 12, wherein the localization device comprises a localization device receiver and with the tracker transmitter and the localization device receiver being configured to communicate using the non-optical communication method, and wherein the tracker comprises one or more inertial sensors configured to generate inertial data, and further comprising:
wirelessly receiving, with the localization device receiver, the generated inertial data from the tracker transmitter using the non-optical communication method.

19. The method of claim 18, wherein the operating parameter manages timing of wireless transmission of the generated inertial data from the tracker transmitter.

20. The method of claim 18, wherein the localization device comprises one or more tracking sensors configured to detect a position of the one or more optical tracking elements for tracking the tracker using the optical communication method, and wherein the operating parameter coordinates both timing of wireless transmission of the generated inertial data from the tracker transmitter and operation of the one or more optical tracking elements of the tracker.

21. The method of claim 18, wherein the operating parameter specifies first and second frequencies for the tracker transmitter and manages switching between the first and second frequencies for the tracker transmitter to implement spectrum diversity.

22. The method of claim 12, wherein:
the optical communication method is further defined as infrared (IR) communication; and
the non-optical communication method is further defined as microwave communication or RF communication.

* * * * *